US012569329B2

(12) United States Patent
Hattori et al.

(10) Patent No.: US 12,569,329 B2
(45) Date of Patent: Mar. 10, 2026

(54) MEDICAL IMAGE PROCESSING APPARATUS, MEDICAL IMAGE PROCESSING METHOD, AND NON-TRANSITORY COMPUTER-READABLE STORAGE MEDIUM

(71) Applicant: CANON MEDICAL SYSTEMS CORPORATION, Tochigi (JP)

(72) Inventors: Chihiro Hattori, Nasushiobara (JP);
Yasuko Fujisawa, Nasushiobara (JP);
Takuya Sakaguchi, Utsunomiya (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 762 days.

(21) Appl. No.: 17/823,324

(22) Filed: Aug. 30, 2022

(65) Prior Publication Data

US 2023/0124908 A1 Apr. 20, 2023

(30) Foreign Application Priority Data

Oct. 14, 2021 (JP) ................................. 2021-169095

(51) Int. Cl.
A61F 2/04 (2013.01)
G06T 7/00 (2017.01)

(52) U.S. Cl.
CPC .............. A61F 2/04 (2013.01); G06T 7/0012 (2013.01); A61F 2002/041 (2013.01)

(58) Field of Classification Search
CPC .... A61F 2/04; A61F 2002/041; G06T 7/0012; G06T 2207/30172; G06T 7/162

(Continued)

(56) References Cited

U.S. PATENT DOCUMENTS

| 4,979,496 A | 12/1990 | Komi |
| 7,369,691 B2 | 5/2008 | Kondo et al. |

(Continued)

FOREIGN PATENT DOCUMENTS

| CN | 109155063 A | * | 1/2019 | ............. A61B 5/055 |
| JP | 1-254135 A | | 10/1989 | |

(Continued)

OTHER PUBLICATIONS

Japanese Office Action issued Apr. 16, 2025 in Japanese Patent Application No. 2021-169095, 5 pages.

(Continued)

*Primary Examiner* — Jennifer Mehmood
*Assistant Examiner* — Eric James Shoemaker
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry is configured to obtain a medical image related to the pancreas. The processing circuitry is configured to extract a pancreas region included in the medical image. The processing circuitry is configured to extract at least one tubular structure region from the inside of the pancreas region. The processing circuitry is configured to identify a first end part and a second end part related to the pancreas on the basis of the pancreas region. The processing circuitry is configured to estimate a primary pancreatic duct centerline of the pancreas on the basis of the tubular structure region, the first end part, and the second end part.

10 Claims, 15 Drawing Sheets

(58) Field of Classification Search
USPC ........................................................ 382/128
See application file for complete search history.

(56) References Cited

U.S. PATENT DOCUMENTS

| | | | | |
|---|---|---|---|---|
| 8,229,186 | B2 * | 7/2012 | Milstein | .................... G06T 7/12 |
| | | | | 382/128 |
| 11,200,976 | B2 | 12/2021 | Mohr et al. | |
| 2004/0249270 | A1 | 12/2004 | Kondo et al. | |
| 2009/0192558 | A1 | 7/2009 | Whitehurst et al. | |
| 2019/0147590 | A1 | 5/2019 | Vikal et al. | |
| 2021/0057081 | A1 | 2/2021 | Mohr et al. | |
| 2024/0112786 | A1 | 4/2024 | Ogasawara et al. | |

FOREIGN PATENT DOCUMENTS

| | | | | | |
|---|---|---|---|---|---|
| JP | 2004518186 | A | * | 6/2004 | ............. G06T 15/08 |
| JP | 2004-283373 | A | | 10/2004 | |
| JP | 2013-43016 | A | | 3/2013 | |
| JP | 2013-169390 | A | | 9/2013 | |
| JP | 2019-528090 | A | | 10/2019 | |
| JP | 2021-30048 | A | | 3/2021 | |
| WO | WO-2022051344 | A1 | * | 3/2022 | ............. A61B 5/743 |
| WO | WO-2022/270150 | A1 | | 12/2022 | |
| WO | WO 2022/270152 | A1 | | 12/2022 | |

OTHER PUBLICATIONS

Japanese Office Action issued Aug. 6, 2025 in Japanese Patent Application No. 2021-169095, 3 pages.

* cited by examiner

FIG.2

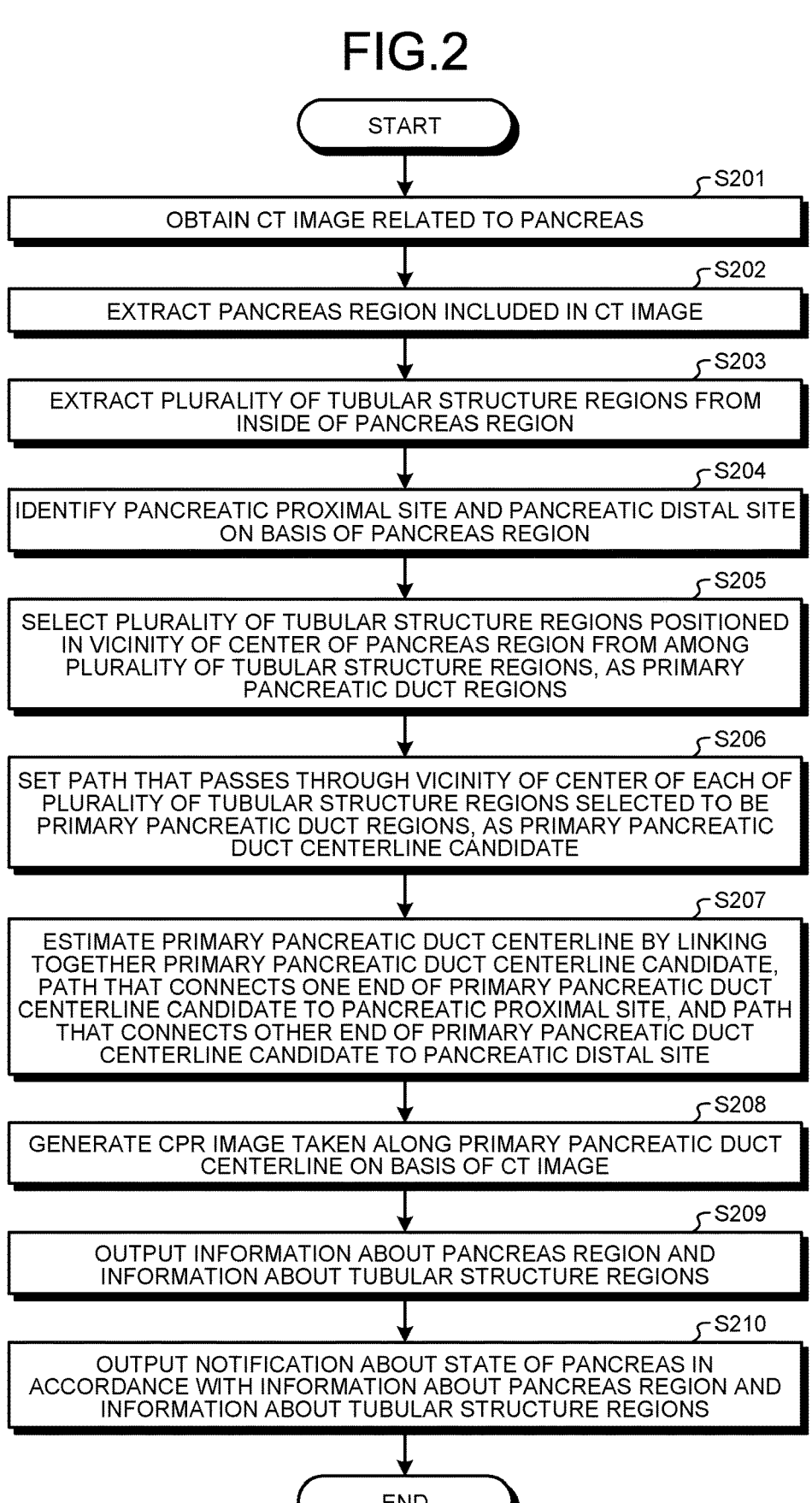

START

S201

OBTAIN CT IMAGE RELATED TO PANCREAS

S202

EXTRACT PANCREAS REGION INCLUDED IN CT IMAGE

S203

EXTRACT PLURALITY OF TUBULAR STRUCTURE REGIONS FROM INSIDE OF PANCREAS REGION

S204

IDENTIFY PANCREATIC PROXIMAL SITE AND PANCREATIC DISTAL SITE ON BASIS OF PANCREAS REGION

S205

SELECT PLURALITY OF TUBULAR STRUCTURE REGIONS POSITIONED IN VICINITY OF CENTER OF PANCREAS REGION FROM AMONG PLURALITY OF TUBULAR STRUCTURE REGIONS, AS PRIMARY PANCREATIC DUCT REGIONS

S206

SET PATH THAT PASSES THROUGH VICINITY OF CENTER OF EACH OF PLURALITY OF TUBULAR STRUCTURE REGIONS SELECTED TO BE PRIMARY PANCREATIC DUCT REGIONS, AS PRIMARY PANCREATIC DUCT CENTERLINE CANDIDATE

S207

ESTIMATE PRIMARY PANCREATIC DUCT CENTERLINE BY LINKING TOGETHER PRIMARY PANCREATIC DUCT CENTERLINE CANDIDATE, PATH THAT CONNECTS ONE END OF PRIMARY PANCREATIC DUCT CENTERLINE CANDIDATE TO PANCREATIC PROXIMAL SITE, AND PATH THAT CONNECTS OTHER END OF PRIMARY PANCREATIC DUCT CENTERLINE CANDIDATE TO PANCREATIC DISTAL SITE

S208

GENERATE CPR IMAGE TAKEN ALONG PRIMARY PANCREATIC DUCT CENTERLINE ON BASIS OF CT IMAGE

S209

OUTPUT INFORMATION ABOUT PANCREAS REGION AND INFORMATION ABOUT TUBULAR STRUCTURE REGIONS

S210

OUTPUT NOTIFICATION ABOUT STATE OF PANCREAS IN ACCORDANCE WITH INFORMATION ABOUT PANCREAS REGION AND INFORMATION ABOUT TUBULAR STRUCTURE REGIONS

END

GALLBLADDER

PANCREAS

FIG.20

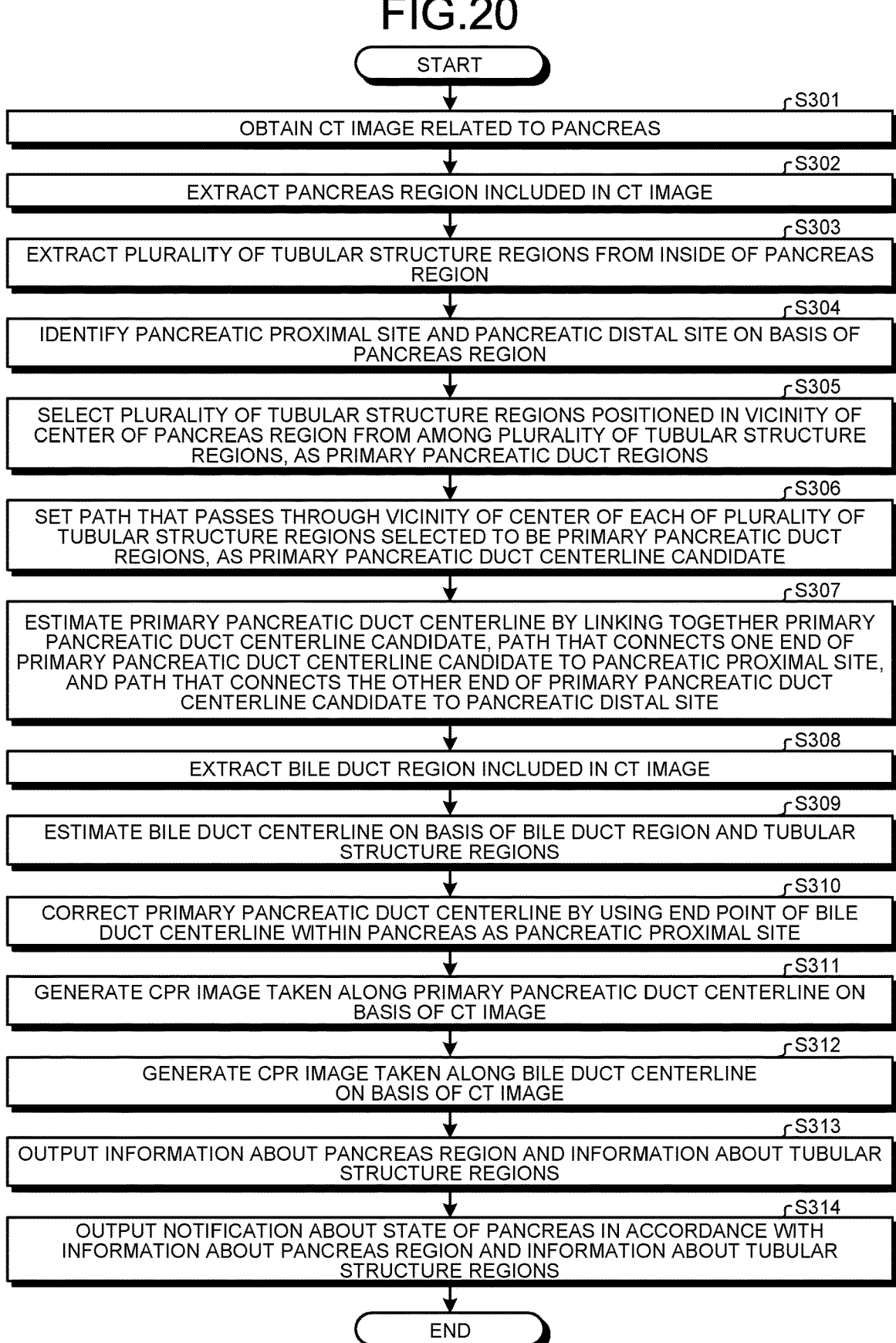

START

S301
OBTAIN CT IMAGE RELATED TO PANCREAS

S302
EXTRACT PANCREAS REGION INCLUDED IN CT IMAGE

S303
EXTRACT PLURALITY OF TUBULAR STRUCTURE REGIONS FROM INSIDE OF PANCREAS REGION

S304
IDENTIFY PANCREATIC PROXIMAL SITE AND PANCREATIC DISTAL SITE ON BASIS OF PANCREAS REGION

S305
SELECT PLURALITY OF TUBULAR STRUCTURE REGIONS POSITIONED IN VICINITY OF CENTER OF PANCREAS REGION FROM AMONG PLURALITY OF TUBULAR STRUCTURE REGIONS, AS PRIMARY PANCREATIC DUCT REGIONS

S306
SET PATH THAT PASSES THROUGH VICINITY OF CENTER OF EACH OF PLURALITY OF TUBULAR STRUCTURE REGIONS SELECTED TO BE PRIMARY PANCREATIC DUCT REGIONS, AS PRIMARY PANCREATIC DUCT CENTERLINE CANDIDATE

S307
ESTIMATE PRIMARY PANCREATIC DUCT CENTERLINE BY LINKING TOGETHER PRIMARY PANCREATIC DUCT CENTERLINE CANDIDATE, PATH THAT CONNECTS ONE END OF PRIMARY PANCREATIC DUCT CENTERLINE CANDIDATE TO PANCREATIC PROXIMAL SITE, AND PATH THAT CONNECTS THE OTHER END OF PRIMARY PANCREATIC DUCT CENTERLINE CANDIDATE TO PANCREATIC DISTAL SITE

S308
EXTRACT BILE DUCT REGION INCLUDED IN CT IMAGE

S309
ESTIMATE BILE DUCT CENTERLINE ON BASIS OF BILE DUCT REGION AND TUBULAR STRUCTURE REGIONS

S310
CORRECT PRIMARY PANCREATIC DUCT CENTERLINE BY USING END POINT OF BILE DUCT CENTERLINE WITHIN PANCREAS AS PANCREATIC PROXIMAL SITE

S311
GENERATE CPR IMAGE TAKEN ALONG PRIMARY PANCREATIC DUCT CENTERLINE ON BASIS OF CT IMAGE

S312
GENERATE CPR IMAGE TAKEN ALONG BILE DUCT CENTERLINE ON BASIS OF CT IMAGE

S313
OUTPUT INFORMATION ABOUT PANCREAS REGION AND INFORMATION ABOUT TUBULAR STRUCTURE REGIONS

S314
OUTPUT NOTIFICATION ABOUT STATE OF PANCREAS IN ACCORDANCE WITH INFORMATION ABOUT PANCREAS REGION AND INFORMATION ABOUT TUBULAR STRUCTURE REGIONS

END

BILE
DUCT

MEDICAL IMAGE PROCESSING APPARATUS, MEDICAL IMAGE PROCESSING METHOD, AND NON-TRANSITORY COMPUTER-READABLE STORAGE MEDIUM

CROSS-REFERENCE TO RELATED APPLICATIONS

This application is based upon and claims the benefit of priority from Japanese Patent Application No. 2021-169095, filed on Oct. 14, 2021; the entire contents of which are incorporated herein by reference.

FIELD

Embodiments described herein relate generally to a medical image processing apparatus, a medical image processing method, and a non-transitory computer-readable storage medium.

BACKGROUND

In the medical field, diagnosing processes and examinations have conventionally been performed on the pancreas by using medical images acquired by medical image diagnosis apparatuses such as X-ray Computed Tomography (CT) apparatuses, Magnetic Resonance Imaging (MRI) apparatuses, and ultrasound diagnosis apparatuses. For example, during diagnosing processes and examinations of the pancreas, a Curved Planar Reconstruction (CPR) image taken along the extending direction of the primary pancreatic duct may be used for evaluating the pancreas itself, searching for cancer, and the like. However, because the primary pancreatic duct is an organ having a very small diameter and thus has low visibility, the primary pancreatic duct rendered in an image is often partially interrupted. As a result, the diagnosing processes and the examinations on the pancreas can be difficult in some situations.

BRIEF DESCRIPTION OF THE DRAWINGS

FIG. 2 is a flowchart illustrating a processing procedure in processes performed by the medical image processing apparatus according to the first embodiment;

FIG. 20 is a flowchart illustrating a processing procedure in processes performed by a medical image processing apparatus according to a second embodiment;

DETAILED DESCRIPTION

A medical image processing apparatus according to an embodiment includes an obtaining unit, a first extracting unit, a second extracting unit, an identifying unit, and an estimating unit. The obtaining unit is configured to obtain a medical image related to the pancreas. The first extracting unit is configured to extract a pancreas region included in the medical image. The second extracting unit is configured to extract at least one tubular structure region from the inside of the pancreas region. The identifying unit is configured to identify a first end part and a second end part related to the pancreas on the basis of the pancreas region. The estimating unit is configured to estimate a primary pancreatic duct centerline of the pancreas on the basis of the tubular structure region, the first end part, and the second end part.

Exemplary embodiments of a medical image processing apparatus, a medical image processing method, and a non-transitory computer-readable storage medium will be explained in detail below, with reference to the accompanying drawings.

First Embodiment

Figure 1:
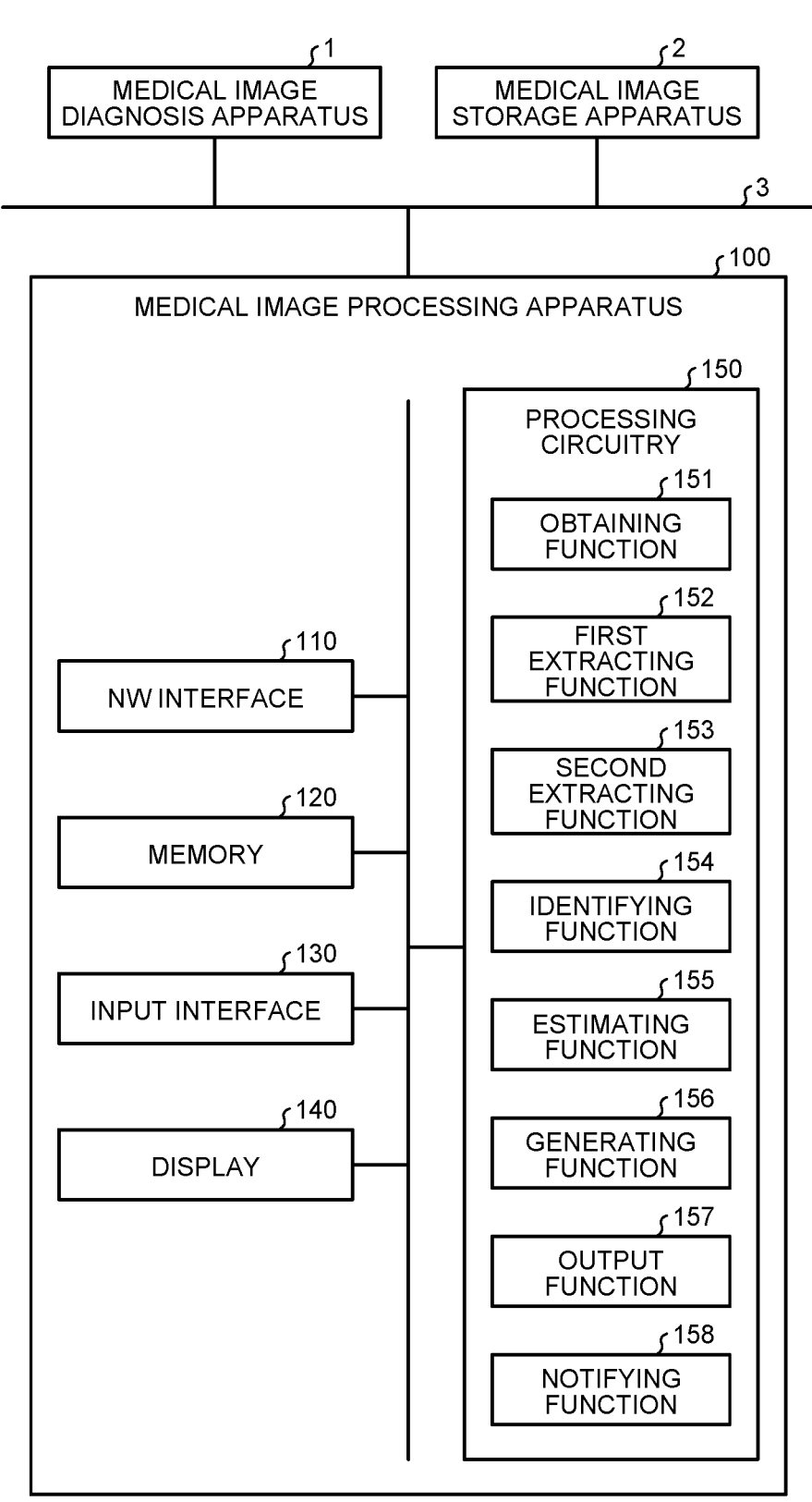
FIG. 1 is a diagram illustrating an exemplary configuration of a medical image processing apparatus according to a first embodiment.

FIG. 1 is a diagram illustrating an exemplary configuration of a medical image processing apparatus according to a first embodiment.

For example, as illustrated in FIG. 1, a medical image processing apparatus 100 according to the present embodiment is connected to a medical image diagnosis apparatus 1 and to a medical image storage apparatus 2 via a network 3, so as to be able to communicate with each other. In addition, the medical image processing apparatus 100 may further be connected to other apparatuses (not illustrated) via the network 3.

The medical image diagnosis apparatus 1 is configured to acquire a medical image related to an examined subject (hereinafter, "patient"). For example, the medical image diagnosis apparatus 1 may be an X-ray computed Tomography (CT) apparatus, a Magnetic Resonance Imaging (MRI) apparatus, an ultrasound diagnosis apparatus, an X-ray diagnosis apparatus, or the like.

The medical image storage apparatus 2 is configured to store therein the medical image acquired by the medical image diagnosis apparatus 1. For example, the medical image storage apparatus 2 is realized by using a computer device such as a Picture Archiving and Communication System (PACS) server and is configured to store the medical image therein in a format compliant with a Digital Imaging and Communications in Medicine (DICOM) scheme.

The medical image processing apparatus 100 is configured to process the medical image related to the patient. More specifically, the medical image processing apparatus 100 is configured to obtain the medical image from either the medical image diagnosis apparatus 1 or the medical image storage apparatus 2 via the network 3 and to process the obtained medical image. For example, the medical image processing apparatus 100 is realized by using a computer device such as a workstation.

For example, the medical image processing apparatus 100 includes a Network (NW) interface 110, a memory 120, an input interface 130, a display 140, and processing circuitry 150.

The NW interface 110 is configured to control transfer of various types of data and communication performed between the medical image processing apparatus 100 and other apparatuses via the network 3. More specifically, the NW interface 110 is connected to the processing circuitry 150 and is configured to transmit data received from the other apparatuses to the processing circuitry 150 and to transmit data received from the processing circuitry 150 to any of the other apparatuses. For example, the NW interface 110 is realized by using a network card, a network adaptor, a Network interface Controller (NIC), or the like.

The memory 120 is configured to store therein various types of data and various types of programs. More specifically, the memory 120 is connected to the processing circuitry 150 and is configured to store therein data received from the processing circuitry 150 and to read and transmit any of the data stored therein to the processing circuitry 150. For example, the memory 120 is realized by using a semiconductor memory element such as a Random Access Memory (RAM) or a flash memory, or a hard disk, an optical disk, or the like.

The input interface 130 is configured to receive operations to input various types of instructions and various types of information from an operator. More specifically, the input interface 130 is connected to the processing circuitry 150 and is configured to convert the input operations received from the operator into electrical signals and to transmit the electrical signals to the processing circuitry 150. For example, the input interface 130 is realized by using a trackball, a switch button, a mouse, a keyboard, a touchpad on which input operations can be performed by touching an operation surface thereof, a touch screen in which a display screen and a touchpad are integrally formed, a contactless input interface using an optical sensor, an audio input interface, and/or the like. In the present disclosure, the input interface 130 does not necessarily have to include physical operation component parts such as a mouse, a keyboard, and/or the like. For instance, possible examples of the input interface 130 include electrical signal processing circuitry configured to receive an electrical signal corresponding to an input operation from an external input device provided separately from the apparatus and to transmit the electrical signal to a controlling circuit.

The display 140 is configured to display various types of information and various types of data. More specifically, the display 140 is connected to the processing circuitry 150 and is configured to display the various types of information and the various types of data received from the processing circuitry 150. For example, the display 140 is realized by using a liquid crystal monitor, a Cathode Ray Tube (CRT) monitor, a touch panel, or the like.

The processing circuitry 150 is configured to perform various types of processes by controlling constituent elements included in the medical image processing apparatus 100. For example, the processing circuitry 150 is configured to perform the various types of processes in accordance with the input operations received from the operator via the input interface 130. Further, for example, the processing circuitry 150 is configured to store any of the data received by the NW interface 110 from other apparatuses into the memory 120. Also, for example, the processing circuitry 150 is configured to transmit any of the data read from the memory 120 to other apparatuses, by transmitting the data to the NW interface 110. In addition, for example, the processing circuitry 150 is configured to cause the display 140 to display any of the data read from the memory 120.

A configuration of the medical image processing apparatus 100 according to the present embodiment has thus been explained. The medical image processing apparatus 100 according to the present embodiment configured as described above has a function of assisting diagnosing processes and examinations performed on the pancreas, on the basis of the medical image acquired by the medical image diagnosis apparatus 1.

For example, during diagnosing processes and examinations of the pancreas, a CPR image taken along the extending direction of the primary pancreatic duct may be used for evaluating the pancreas itself, searching for cancer, and the like. However, because the primary pancreatic duct is an organ having a very small diameter (usually less than 3 mm for a healthy primary pancreatic duct) and thus has low visibility, the primary pancreatic duct rendered in an image is often partially interrupted. As a result, the diagnosing processes and the examinations on the pancreas can be difficult in some situations.

More specifically, at the time of generating the CPR image taken along the extending direction of the primary pancreatic duct, it is necessary to set, in advance, a primary pancreatic duct centerline extending through the entire pancreas. However, when the primary pancreatic duct centerline is set by performing image processing, a number of problems may arise. For example, the image processing related to the pancreas has problems as follows: It is difficult to accurately extract the region of the pancreas when trying to grasp the entire pancreas; it is difficult to extract a pancreatic duct region extending throughout the entire pancreas, because image brightness levels within pancreatic ducts are uneven; it is difficult, when cancer is present, to detect the primary pancreatic duct because the primary pancreatic duct may be interrupted by the cancer; and it is difficult in a CT image to distinguish a bile duct from pancreatic ducts, simply by extracting a low absorption region from the inside of a pancreas region.

For this reason, generally speaking, a primary pancreatic duct centerline is manually set, but the setting process could take a lot of trouble and time, because of problems similar to those of the image processing described above. In addition, there is another problem where manually setting a primary pancreatic duct centerline has low reproducibility.

In relation to the above, techniques have been developed in recent years by which an organ is detected from an image with the use of Artificial Intelligence (AI). However, because of low visibility, detecting the primary pancreatic duct yields too many variations. It is therefore considered difficult to use AI for setting a primary pancreatic duct centerline extending through the entire pancreas.

To cope with the circumstances described above, the medical image processing apparatus 100 according to the present embodiment is configured so as to be able to easily perform diagnosing processes and examinations on the pancreas, even when the primary pancreatic duct rendered in an image is partially interrupted.

More specifically, the medical image processing apparatus 100 includes, as processing functions of the processing circuitry 150, an obtaining function 151, a first extracting function 152, a second extracting function 153, an identifying function 154, an estimating function 155, a generating function 156, an output function 157, and a notifying function 158.

In this situation, the obtaining function 151 is an example of an obtaining unit. The first extracting function 152 is an example of a first extracting unit. The second extracting function 153 is an example of a second extracting unit. The identifying function 154 is an example of an identifying unit. The estimating function 155 is an example of an estimating unit. The generating function 156 is an example of a generating unit. The output function 157 is an example of an output unit. The notifying function 158 is an example of a notifying unit.

The obtaining function 151 is configured to obtain a medical image related to the pancreas. Further, the first extracting function 152 is configured to extract a pancreas region included in the medical image obtained by the obtaining function 151. In addition, the second extracting function 153 is configured to extract at least one tubular structure region from the inside of the pancreas region obtained by the first extracting function 152.

Further, the identifying function 154 is configured to identify a first end part and a second end part related to the pancreas, on the basis of the pancreas region extracted by the first extracting function 152. Also, the estimating function 155 is configured to estimate a primary pancreatic duct centerline of the pancreas, on the basis of the tubular structure region extracted by the second extracting function 153 and the first end part and the second end part identified by the identifying function 154. Further, the generating function 156 is configured to generate a CPR image taken along the primary pancreatic duct centerline estimated by the estimating function 155, on the basis of the medical image obtained by the obtaining function 151.

Furthermore, the output function 157 is configured to output information about the pancreas region extracted by the first extracting function 152 and information about the tubular structure region extracted by the second extracting function 153. In addition, the notifying function 158 is configured to output a notification about a state of the pancreas, in accordance with the information about the pancreas region extracted by the first extracting function 152 and the information about the tubular structure region extracted by the second extracting function 153.

In this situation, for example, the processing circuitry 150 is realized by using a processor. In that situation, for example, the processing functions of the processing circuitry 150 are stored in the memory 120 in the form of computer-executable programs. Further, the processing circuitry 150 is configured to realize the functions corresponding to the programs, by reading and executing the programs stored in the memory 120. In other words, the processing circuitry 150 that has read the programs has the processing functions illustrated in FIG. 1.

Next, the processing functions of the processing circuitry 150 according to the present embodiment will be described in detail, while referring to specific examples. In the following sections, an example will be explained in which the medical image to be processed is a CT image acquired by an X-ray CT apparatus, whereas the first end part related to the pancreas is a pancreatic proximal site, while the second end part is a pancreatic distal site.

FIG. 2 is a flowchart illustrating a processing procedure in processes performed by the medical image processing apparatus 100 according to the first embodiment. FIGS. 3 to 19 are drawings illustrating examples of the processes performed by the medical image processing apparatus 100 according to the first embodiment.

For example, as illustrated in FIG. 2, at first, the obtaining function 151 obtains the CT image related to the pancreas (step S201 in FIG. 2).

More specifically, the obtaining function 151 is configured to obtain the CT image to be processed, which is three-dimensional, from either the medical image diagnosis apparatus 1 or the medical image storage apparatus 2 via the NW interface 110 and the network 3. In this situation, the three-dimensional CT image may be a three-dimensional image (volume data) corresponding to a three-dimensional region including the pancreas or may be a plurality of two-dimensional images (multi-slice data) corresponding to a plurality of cross-sectional planes of the same pancreas. Further, the obtaining function 151 is configured to store the obtained CT image into the memory 120.

For example, the obtaining function 151 is configured to receive, from the operator, an operation to designate the CT image to be processed via the input interface 130 and to obtain the designated CT image from either the medical image diagnosis apparatus 1 or the medical image storage apparatus 2.

Figure 3:
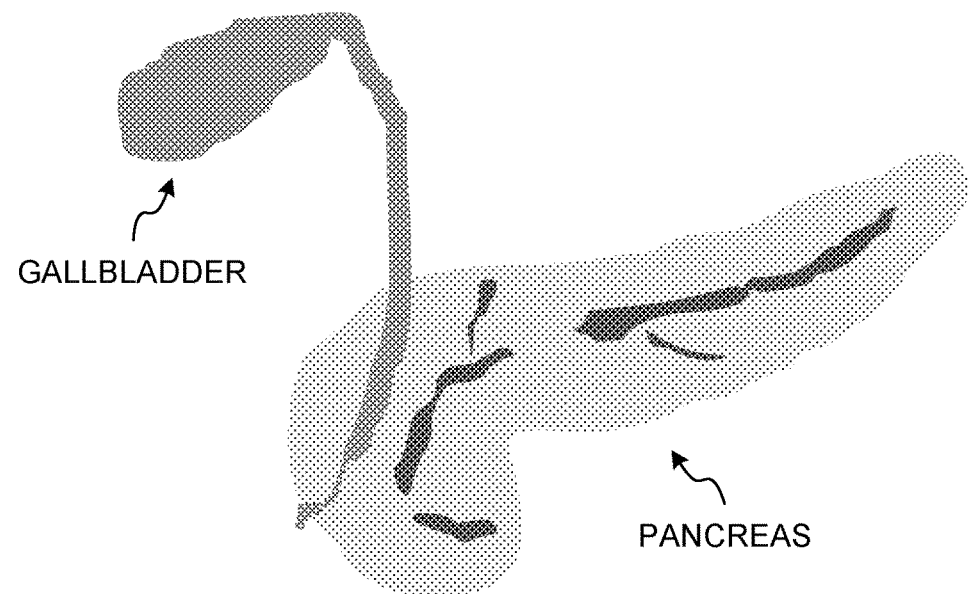
FIG. 3 is a drawing illustrating examples of the processes performed by the medical image processing apparatus according to the first embodiment.

For example, as illustrated in FIG. 3, the obtaining function 151 is configured to obtain the CT image rendering the pancreas and the gallbladder.

Subsequently, the first extracting function 152 extracts the pancreas region included in the CT image obtained by the obtaining function 151 (step S202 in FIG. 2).

More specifically, the first extracting function 152 is configured to read the CT image obtained by the obtaining function 151 from the memory 120 and to extract the pancreas region included in the read CT image.

For example, the first extracting function 152 is configured, at first, to estimate an approximate presence range of the pancreas included in the CT image. For example, by using AI, the first extracting function 152 is configured to estimate the presence range of the pancreas, on the basis of organs (the stomach, the duodenum, the spleen, the small intestine, and the large intestine) surrounding the pancreas among the abdominal organs and blood vessels and ducts (the splenic artery and vein, the superior mesenteric artery and vein, the bile duct, and the hepatic artery). In another example, the first extracting function 152 may estimate a presence range of the pancreas itself on the basis of anatomical landmarks.

After that, the first extracting function 152 is configured to extract the pancreas region from the approximate presence range of the pancreas. For example, the first extracting function 152 is configured to estimate the pancreas region, by approximately segmenting the pancreas while using a segmentation-purpose learning model (typically, a U-Net-based 3D-CNN or an nnU-Net) in the region of the approximate presence range of the pancreas, for example, and subsequently shaping the extracting region in a post-processing process. For example, the first extracting function 152 may be configured to delete subregions through a volume threshold value process and to subsequently correct a contour through a graph cut process performed as the post-processing process.

By extracting the pancreas region through the process described above, it is possible to extract the region of the entire pancreas with a high level of precision.

Subsequently, the second extracting function 153 extracts the plurality of tubular structure regions from the inside of the pancreas region obtained by the first extracting function 152 (step S203 in FIG. 2).

More specifically, the second extracting function 153 is configured to extract the plurality of tubular structure regions, by extracting low absorption regions from the inside of the pancreas region. As a result, pancreatic duct regions that are visually recognizable in the image are extracted as the plurality of tubular structure regions.

Figure 4:
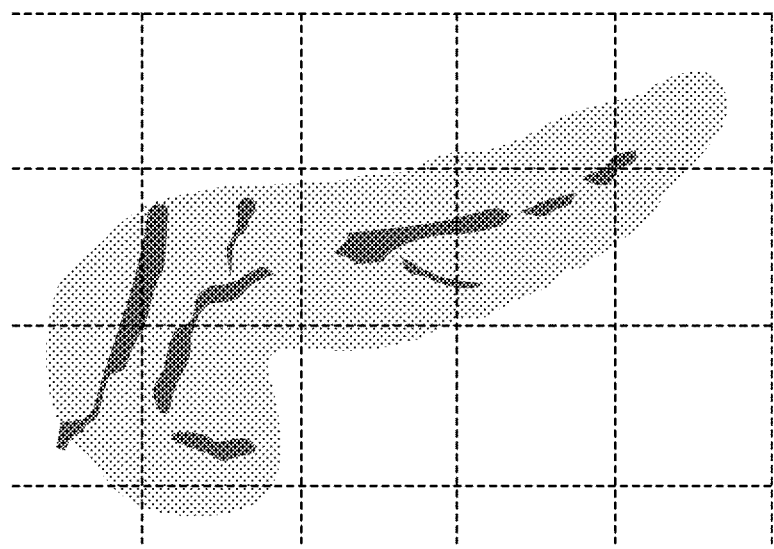
FIG. 4 is another drawing illustrating the examples of the processes performed by the medical image processing apparatus according to the first embodiment.

For example, as illustrated in FIG. 4, the second extracting function 153 is configured to separate the pancreas region into a plurality of zones and to further segment, with respect to each of the zones, a region which is equal to or larger than a predetermined size and in which pixel values are relatively lower than those in the surroundings. Further, the second extracting function 153 is configured to extract the plurality of tubular structure regions, by connecting and growing the segmented regions in adjacently-positioned or overlapping zones. Alternatively, for example, the second extracting function 153 may extract the plurality of tubular structure regions, by segmenting the pancreatic duct regions while using a U-Net-based 3D-CNN or an nnU-Net that learned pancreatic duct regions from the inside of pancreas regions.

Subsequently, the identifying function 154 identifies the pancreatic proximal site and the pancreatic distal site, on the basis of the pancreas region extracted by the first extracting function 152 (step S204 in FIG. 2).

For example, on the basis of anatomical landmarks, the identifying function 154 is configured to identify a tip end of a pancreatic head part or a (or the major) duodenal papilla in the pancreas region as the pancreatic proximal site and to identify a tip end of a pancreatic tail part as the pancreatic distal site. In another example, the identifying function 154 may be configured to identify a minimum point on the X-coordinate in the pancreas region as the pancreatic proximal site and to identify a maximum point as the pancreatic distal site. In yet another example, the identifying function 154 may be configured to define a center-of-gravity point of the pancreas region as a reference point, so as to identify either a pixel closest to a leg or a point positioned furthest to the right among the surface points in the pancreas region positioned on the pancreatic head part side (the right side in the body) relative to the reference point as the pancreatic proximal site and to identify a pixel farthest from the reference point among the surface points in the pancreas region positioned on the pancreatic tail part side (the left shoulder side) relative to the reference point as the pancreatic distal site.

Subsequently, the estimating function 155 is configured to select, from among the plurality tubular structure regions extracted by the second extracting function 153, a plurality of tubular structure regions positioned in the vicinity of the center of the pancreas region as primary pancreatic duct regions and to further estimate a primary pancreatic duct centerline of the pancreas, on the basis of the primary pancreatic duct regions as well as the pancreatic proximal site and the pancreatic distal site identified by the identifying function 154.

Figure 5:
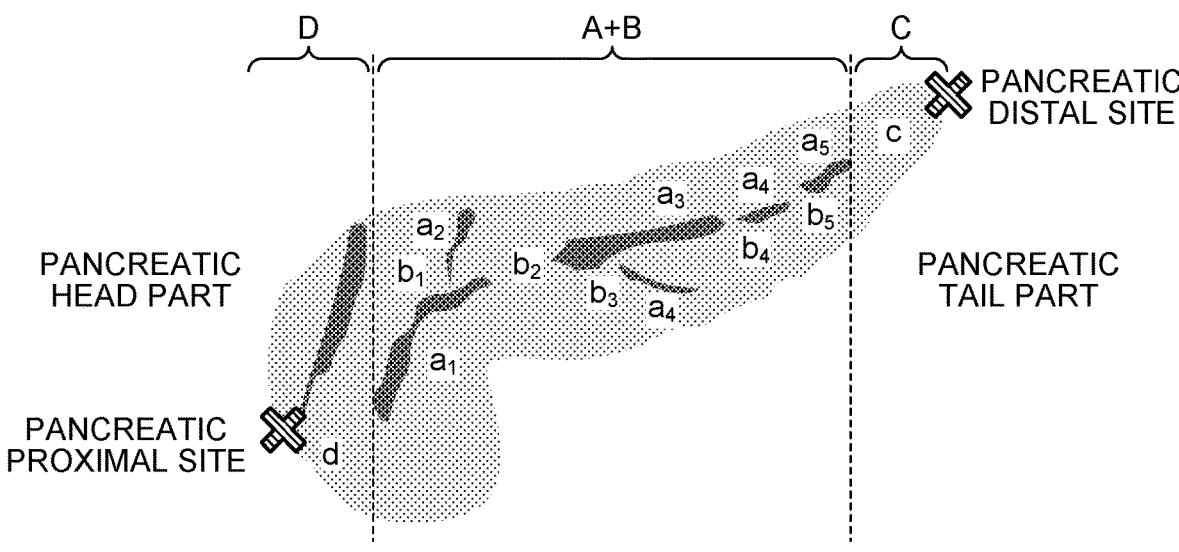
FIG. 5 is yet another drawing illustrating the examples of the processes performed by the medical image processing apparatus according to the first embodiment.

For example, as illustrated in FIG. 5, the estimating function 155 is configured to perform a process of estimating a centerline in a range (A+B in FIG. 5) including a plurality of tubular structure regions (pancreatic duct regions visually recognizable in the image) "$a_i$" (where i=1 to n) and regions "$b_j$" (where j=1 to m) positioned therebetween and to further estimate a line connecting a primary pancreatic duct centerline candidate obtained as a result of this process to the pancreatic proximal site and to the pancreatic distal site as the primary pancreatic duct centerline.

More specifically, at first, the estimating function 155 selects, from among the plurality of tubular structure regions extracted by the second extracting function 153, a plurality of tubular structure regions positioned in the vicinity of the center of the pancreas region, as the primary pancreatic duct regions (step S205 in FIG. 2).

For example, on the assumption that the pancreas region is a tubular structure of which the end points (the bottom faces) are at the position of the pancreatic proximal site and the position of the pancreatic distal site, the estimating function 155 is configured to select each of the plurality of tubular structure regions positioned in the vicinity of the center of the pancreas region as a primary pancreatic duct region.

Figure 6:
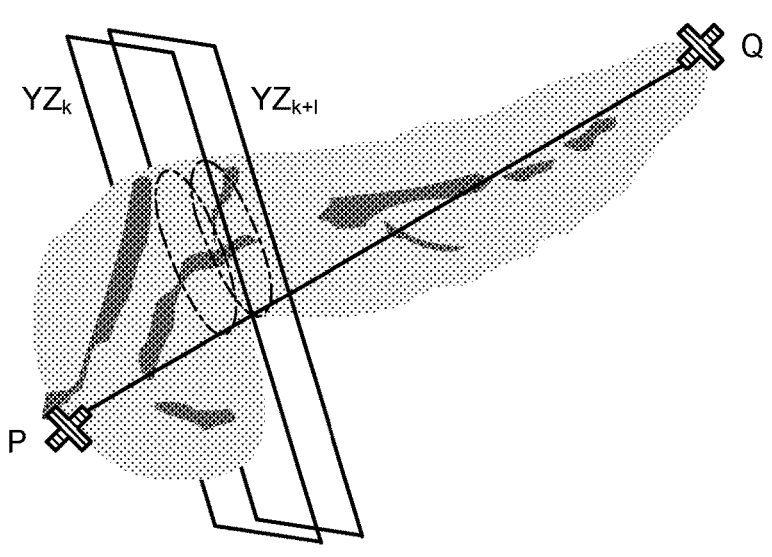
FIG. 6 is yet another drawing illustrating the examples of the processes performed by the medical image processing apparatus according to the first embodiment.

For example, as illustrated in FIG. 6, the estimating function 155 is configured to obtain, with respect to the pancreas region, cross-sectional planes YZ each of which is perpendicular to a coronal plane and includes a line normal to the vector of a line segment PQ connecting the position of the pancreatic proximal site to the position of the pancreatic distal site, the cross-sectional planes YZ being arranged on the line segment PQ at regular intervals. As a result, the plurality of cross-sectional plane YZ ($YZ_k$, $YZ_{k+1}$, and so on, in FIG. 6) are obtained along the line segment PQ. Further, from among all the obtained cross-sectional planes YZ, the estimating function 155 is configured to identify certain tubular structure regions in which the position of the cross-section center-of-gravity is within a predetermined distance from the cross-section center-of-gravity of the pancreas region and to further select the identified tubular structure regions as the primary pancreatic duct regions. In another example, from among all the cross-sectional planes YZ, the estimating function 155 may identify certain tubular structure regions in which the cross-section center-of-gravity is positioned apart from the edge of a cross-section of the pancreas region (the surface of the pancreas region) by a predetermined distance or longer and to further select the identified tubular structure regions as the primary pancreatic duct regions.

Figure 7:
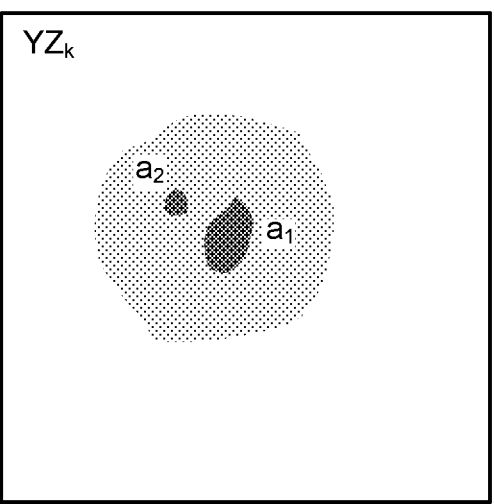
FIG. 7 is yet another drawing illustrating the examples of the processes performed by the medical image processing apparatus according to the first embodiment.
Figure 8:
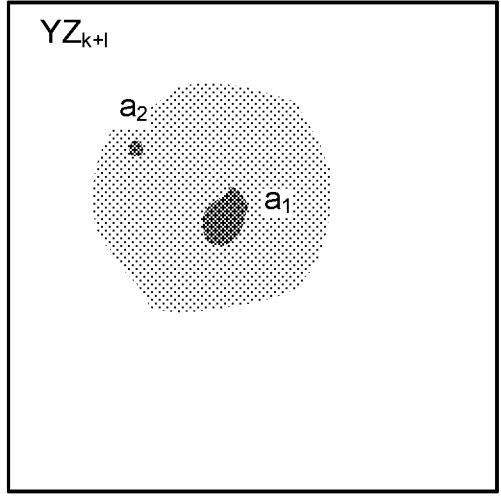
FIG. 8 is yet another drawing illustrating the examples of the processes performed by the medical image processing apparatus according to the first embodiment.

For example, let us discuss a situation in which, with respect to two tubular structure regions "$a_1$" and "$a_2$", the cross-sectional plane $YZ_k$ illustrated in FIG. 7 is obtained at a position k on the line segment PQ, whereas the cross-sectional plane $YZ_{k+1}$ illustrated in FIG. 8 is obtained at a position k+1 which is on the line segment PQ and is positioned apart from the position k by a predetermined distance (e.g., 10 mm).

In this situation, the estimating function 155 is configured to select the tubular structure region "$a_1$" as a primary pancreatic duct region because, for each of the cross-sectional planes $YZ_k$ and $YZ_{k+1}$, the cross-section center-of-gravity is within the predetermined distance (e.g., one fourth of the maximum cross-sectional diameter of the pancreas region) from the cross-section center-of-gravity (indicated with an x) of the pancreas region. In contrast, the estimating function 155 is configured not to select the tubular structure region "$a_2$" as a primary pancreatic duct region because, for the cross-sectional plane $YZ_k$, the cross-section center-of-gravity is within the predetermined distance (e.g., one fourth of the maximum cross-sectional diameter of the pancreas region) from the cross-section center-of-gravity (indicated with an x) of the pancreas region, but for the cross-sectional plane $YZ_{k+1}$, the cross-section center-of-gravity is not within the predetermined distance (e.g., one fourth of the maximum cross-sectional diameter of the pancreas region) from the cross-section center-of-gravity (indicated with an x) of the pancreas region.

In another example, the estimating function 155 may be configured to select the tubular structure region "$a_1$" as a primary pancreatic duct region because, for each of the cross-sectional planes $YZ_k$ and $YZ_{k+1}$, the cross-section center-of-gravity is positioned apart from the edge of the cross-section of the pancreas region by the predetermined distance (e.g., one sixth of the maximum cross-sectional diameter of the pancreas region) or longer. In contrast, the estimating function 155 may be configured not to select the tubular structure region "$a_2$" as a primary pancreatic duct region because, for the cross-sectional plane $YZ_k$, the cross-section center-of-gravity is positioned apart from the edge of the cross-section of the pancreas region by the predetermined distance (e.g., one sixth of the maximum cross-sectional diameter of the pancreas region) or longer, but for the cross-sectional plane $YZ_{k+1}$, the cross-section center-of-gravity is not positioned apart from the edge of the cross-section of the pancreas region by the predetermined distance (e.g., one sixth of the maximum cross-sectional diameter of the pancreas region) or longer.

For example, when the plurality of tubular structure regions are extracted by extracting the low absorption regions from the inside of the pancreas region as explained above, the extracted tubular structure regions also include bile duct regions. However, by selecting only the tubular structure regions that are positioned in the vicinity of the center of the pancreas region as the primary pancreatic duct regions, it is possible to exclude the bile duct regions, which extend up to the surface of the pancreas, from the primary pancreatic duct regions.

After that, the estimating function 155 sets a path that passes through the vicinity of the center of each of the plurality of tubular structure regions selected to be the primary pancreatic duct regions, as the primary pancreatic duct centerline candidate (step S206 in FIG. 2).

Figure 9:
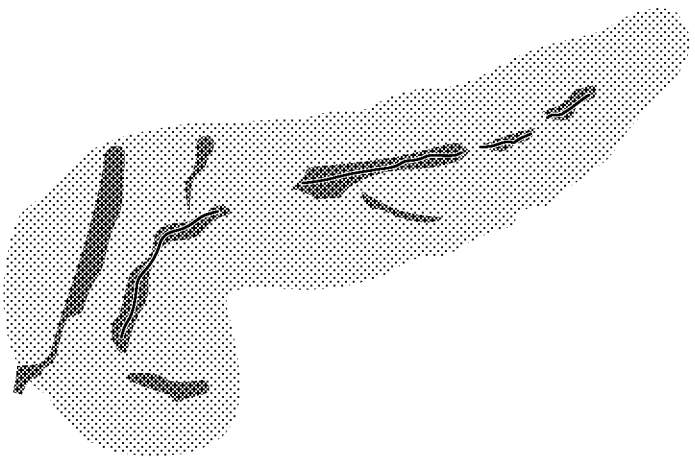
FIG. 9 is yet another drawing illustrating the examples of the processes performed by the medical image processing apparatus according to the first embodiment.

For example, as illustrated in FIG. 9, at first, the estimating function 155 is configured to estimate a centerline of each of the plurality of tubular structure regions "$a_i$" (where i=1 to n). For example, the estimating function 155 is configured to estimate the centerline of each of the tubular structure regions, by making the tubular structure regions into thin lines. Alternatively, the estimating function 155 may estimate the centerline of each of the tubular structure regions, by obtaining a sequence of points including a plurality of points on which weights are varied with respect to the distances from the surface of the region, so as to pass through the center of the tubular structure region.

Subsequently, with regard to the region "$b_j$" (where j=1 to m) that are positioned between the tubular structure regions and were not segmented, the estimating function 155 is configured to estimate a path that connects together the centerlines of the preceding and following tubular structure regions "$a_1$". In this situation, for example, the estimating function 155 is configured to change the process used for estimating the path, depending on the distance between the end points of the tubular structure regions preceding and following the region "$b_j$" which was not segmented.

For example, when the distance between the end points of the preceding and following tubular structure regions is a short distance equal to or shorter than a predetermined length (e.g., 15 mm), the estimating function 155 is configured to estimate a path by connecting the centerlines of the preceding and following tubular structure regions by the shortest distance.

In contrast, when the distance between the end points of the preceding and following tubular structure regions is a long distance exceeding the predetermined length (e.g., 15 mm), the estimating function 155 is configured, for example, to estimate a path by taking into account the shape of a tubular structure $B_j$ included in the region "$b_j$" which was not segmented and the centerlines of the preceding and following tubular structure regions.

Figure 10:
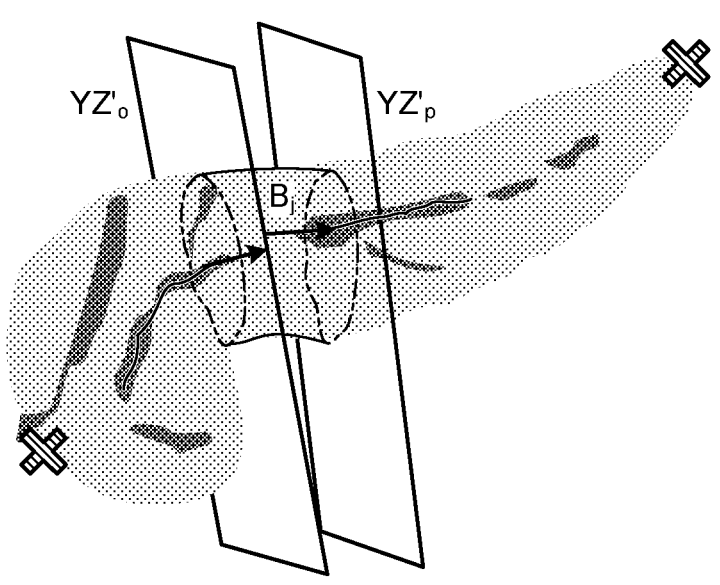
FIG. 10 is yet another drawing illustrating the examples of the processes performed by the medical image processing apparatus according to the first embodiment.
Figure 11:
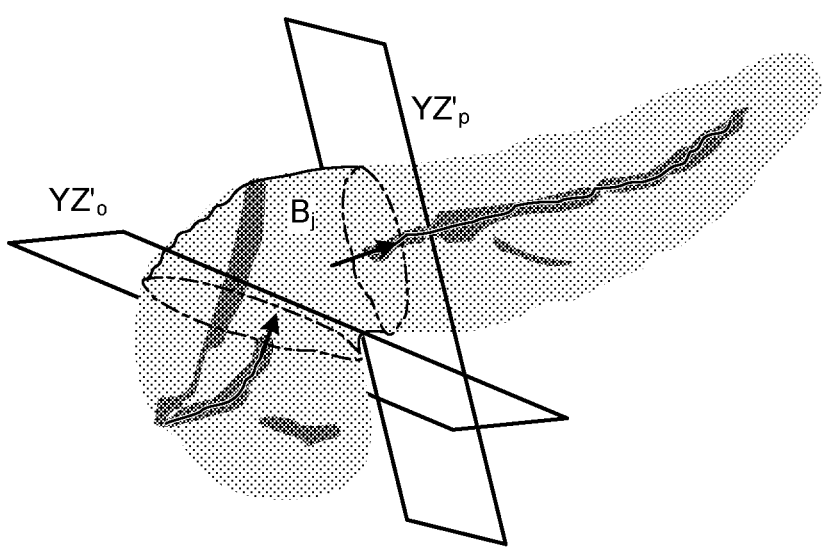
FIG. 11 is yet another drawing illustrating the examples of the processes performed by the medical image processing apparatus according to the first embodiment.

In this situation, for example, as illustrated in FIGS. 10 and 11, the tubular structure $B_j$ is the pancreas region in the range sandwiched between: a cross-sectional plane $YZ'_o$ which is perpendicular to a coronal plane and includes a line normal to a streamline vector at a tip end "o" of the centerline of the preceding tubular structure region positioned on the pancreatic tail part side; and another cross-sectional plane $YZ'_p$ which is perpendicular to a coronal plane and includes a line normal to a streamline vector at a tip end "p" of the centerline of the following tubular structure region positioned on the pancreatic head part side.

For example, from inside of the tubular structure $B_j$, the estimating function 155 is configured to obtain a sequence of points including a plurality of points on which the weights are varied with respect to the distances from the surface of the tubular structure $B_j$ and the distances from the end point of the centerlines of the preceding and following tubular structure regions, depending on the curvature of the tubular structure $B_j$. Further, the estimating function 155 is configured to estimate the path that connects together the centerlines of the preceding and following tubular structure regions, by performing a spline curve approximation on the obtained sequence of points and sequences of points on the centerlines of the preceding and following tubular structure regions.

Figure 12:
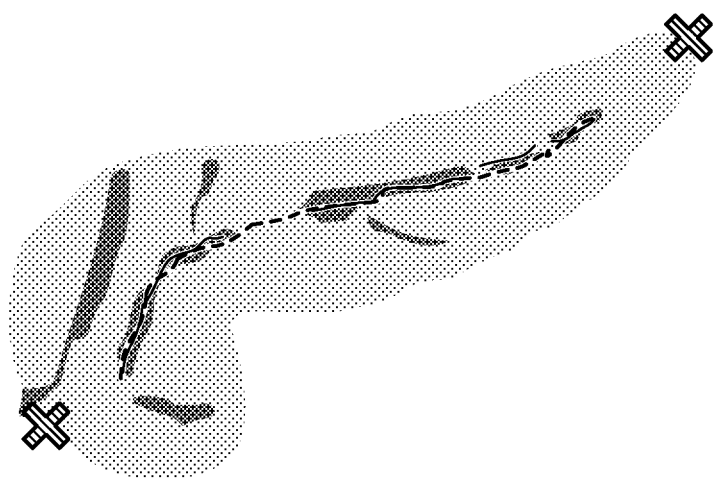
FIG. 12 is yet another drawing illustrating the examples of the processes performed by the medical image processing apparatus according to the first embodiment.

Subsequently, as illustrated in FIG. 12, for example, the estimating function 155 is configured to obtain a path that passes through the vicinity of the center of each of the plurality of tubular structure regions "$a_1$" selected as the primary pancreatic duct regions, by connecting the estimated centerlines of the tubular structure regions "$a_1$" with the paths that connect together the centerlines of the tubular structure regions "at" and is configured to further set the obtained path as the primary pancreatic duct centerline candidate.

Figure 13:
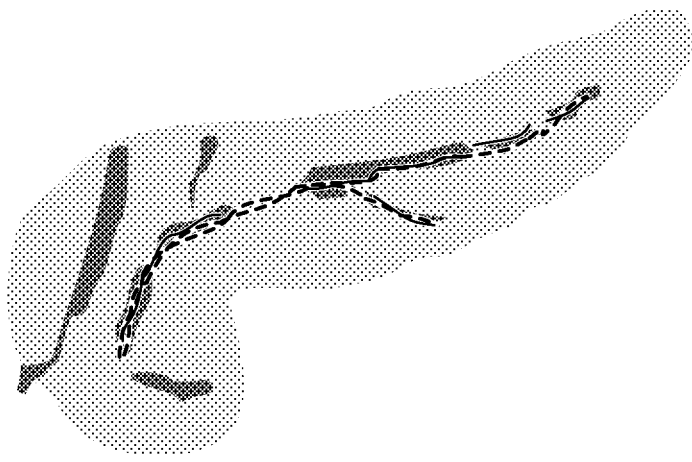
FIG. 13 is yet another drawing illustrating the examples of the processes performed by the medical image processing apparatus according to the first embodiment.

In this situation, as illustrated in FIG. 13, for example, when the path passing through the vicinity of the center of each of the plurality of tubular structure regions "$a_1$" selected as the primary pancreatic duct regions has a tree-like structure having a plurality of branches, the estimating function 155 is configured to set the longest branch extending in the direction connecting the pancreatic proximal site to the pancreatic distal site within the tree-like structure as the primary pancreatic duct centerline candidate.

After that, the estimating function 155 estimates the primary pancreatic duct centerline, by linking together the primary pancreatic duct centerline candidate, a path that connects one end of the primary pancreatic duct centerline candidate to the pancreatic proximal site, and a path that connects the other end of the primary pancreatic duct centerline candidate to the pancreatic distal site (step S207 in FIG. 2).

For example, at first, with regard to the region of the pancreatic tail part (C in FIG. 5), the estimating function 155 is configured to estimate a path that connects the position of the pancreatic distal site to the end point of the centerline of the tubular structure region "$a_n$" positioned closest to the position of the pancreatic distal site. In this situation, for example, the estimating function 155 is configured to change the process used for estimating the path, depending on the distance between the position of the pancreatic distal site and the end point of the centerline of the tubular structure region "$a_n$".

For example, when the distance between the position of the pancreatic distal site and the end point of the centerline of the tubular structure region "$a_n$" is a short distance equal to or shorter than a predetermined length (e.g., 15 mm), the estimating function 155 is configured to estimate a path that connects the position of the pancreatic distal site to the end point of the centerline of the tubular structure region "$a_n$" by the shortest distance.

In contrast, when the distance between the position of the pancreatic distal site and the end point of the centerline of the tubular structure region "$a_n$" is a long distance exceeding the predetermined length (e.g., 15 mm), the estimating function 155 is configured, for example, to estimate a path while taking into account the shape of a tubular structure "c" representing the pancreatic distal site and the centerline of the tubular structure region "$a_n$".

Figure 14:
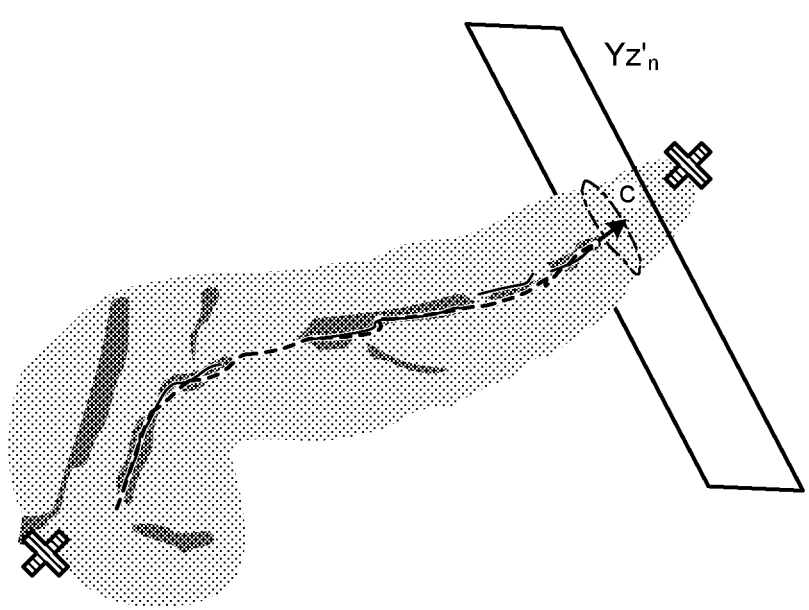
FIG. 14 is yet another drawing illustrating the examples of the processes performed by the medical image processing apparatus according to the first embodiment.

In this situation, as illustrated in FIG. 14, for example, the tubular structure "c" is the pancreas region positioned on the pancreatic tail part side separated by a cross-sectional plane $YZ'_n$ which is perpendicular to a coronal plane and includes a line normal to a streamline vector at the pancreatic-tail-side tip end of the centerline of the tubular structure region "$a_n$" positioned closest to the position of the pancreatic distal site.

For example, from inside of the tubular structure "c", the estimating function 155 is configured to estimate the path that connects the position of the pancreatic distal site to the end point of the centerline of the tubular structure region "$a_n$", by obtaining a sequence of points including a plurality of points on which weights are varied with respect to the distances from the surface of the tubular structure "c" and the distances from the end point of the centerline of the tubular structure region "$a_n$", depending on the curvature of the tubular structure "c".

Figure 15:
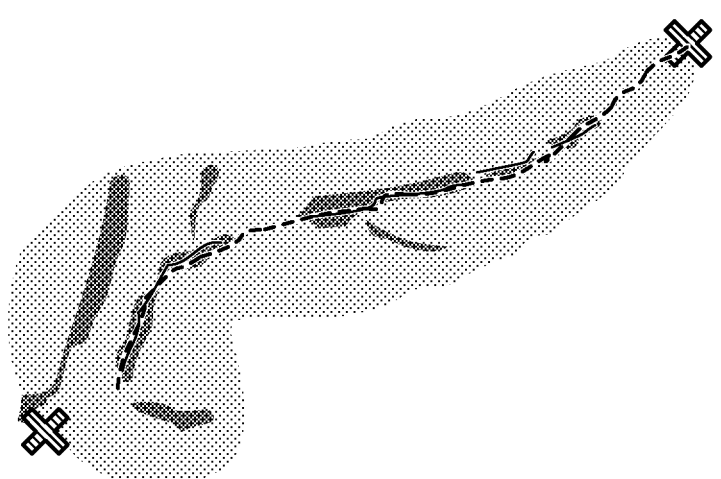
FIG. 15 is yet another drawing illustrating the examples of the processes performed by the medical image processing apparatus according to the first embodiment.

After that, as illustrated in FIG. 15, for example, the estimating function 155 is configured to estimate the path that continues to the end point of the primary pancreatic duct centerline candidate to the pancreatic distal site, by performing a spline curve approximation on the sequence of points obtained as the path that connects the position of the pancreatic distal site to the end point of the centerline of the tubular structure region "$a_n$" and a sequence of points of the centerlines of the primary pancreatic duct centerline candidate.

Subsequently, with regard to the region of the pancreatic head part (D in FIG. 5), the estimating function 155 is configured to estimate a path that connects the position of the pancreatic proximal site to an end point of the centerline of the tubular structure regions "$a_1$" positioned closest to the pancreatic proximal site. In this situation, for example, the estimating function 155 is configured to change the process used for estimating the path, depending on the distance between the position of the pancreatic proximal site and the end point of the centerline of the tubular structure region "$a_1$".

For example, when the distance between the position of the pancreatic proximal site and the end point of the centerline of the tubular structure region "$a_1$" is a short distance equal to or shorter than a predetermined length (e.g., 15 mm), the estimating function 155 is configured to estimate a path that connects the position of the pancreatic proximal site to the end point of the centerline of the tubular structure region "$a_1$" by the shortest distance.

In contrast, when the distance between the position of the pancreatic proximal site and the end point of the centerline of the tubular structure region "$a_1$" is a long distance exceeding the predetermined length (e.g., 15 mm), the estimating function 155 is configured, for example, to estimate a path that connects the position of the pancreatic proximal site to the end point of the centerline of the tubular structure region "$a_1$", by identifying a coefficient of a spline curve on the basis of a sequence of points representing a centerline extended from the centerline of the tubular structure region "$a_1$" to the pancreatic distal site and the position of the pancreatic proximal site and further performing an extrapolation while using an expression of the identified spline curve. For example, the estimating function 155 may estimate the path by re-evaluating a result of a spline approximation, while taking into account the distances from the surface of a tubular structure "d".

Figure 16:
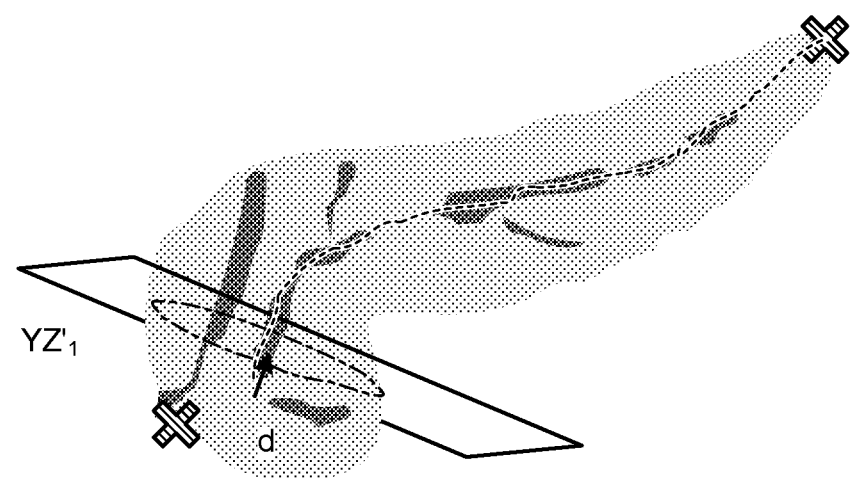
FIG. 16 is yet another drawing illustrating the examples of the processes performed by the medical image processing apparatus according to the first embodiment.

In this situation, as illustrated in FIG. 16, for example, the tubular structure "d" is the pancreas region positioned on the pancreatic head part side separated by a cross-sectional plane $YZ'_1$ which is perpendicular to a coronal plane and includes a line normal to a streamline vector at the pancreatic-head-side tip end of the centerline of the tubular structure region "$a_1$" positioned closest to the position of the pancreatic proximal site.

Figure 17:
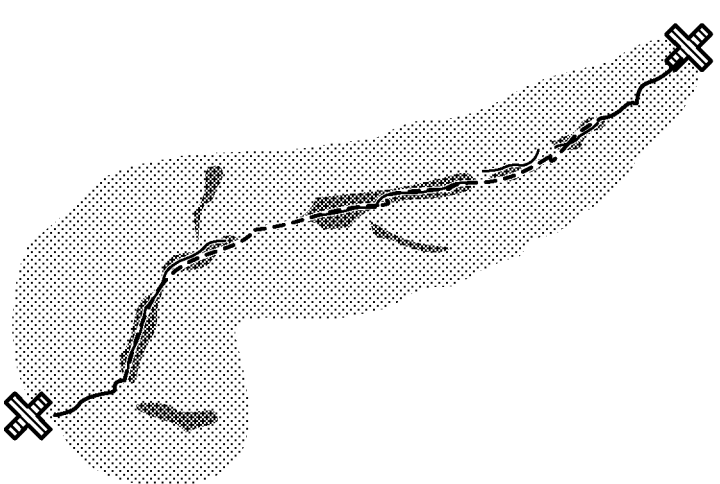
FIG. 17 is yet another drawing illustrating the examples of the processes performed by the medical image processing apparatus according to the first embodiment.

Further, as illustrated in FIG. 17, for example, the estimating function 155 is configured to estimate the primary pancreatic duct centerline extending through the entire pancreas, by linking the path that connects the position of the pancreatic proximal site to the end point of the centerline of the tubular structure region "$a_1$", to the path that continues to the end point of the previously-estimated primary pancreatic duct centerline candidate to the pancreatic distal site.

In this situation, methods that can be used by the estimating function 155 to estimate the primary pancreatic duct centerline extending through the entire pancreas are not limited to the example described above. For instance, the estimating function 155 may estimate the primary pancreatic duct centerline, by estimating the centerline of each of the plurality of tubular structure regions "$a_1$" (where i=1 to n), subsequently performing a spline curve approximation to set a path that passes through core points on the centerlines of the tubular structure region, as well as the position of the pancreatic proximal site and the position of the pancreatic distal site, and further identifying a coefficient of the spline curve that makes the length of the path shortest.

In another example, the estimating function 155 may estimate the primary pancreatic duct centerline, by using a trained model constructed so as to receive an input of a core point on the centerline of each of the plurality of tubular structure regions, as well as the position of a pancreatic proximal site and the position of a pancreatic distal site and to output information about a primary pancreatic duct centerline that corresponds thereto. In that situation, the trained model is generated in advance by using a machine learning method such as deep learning and stored in the memory 120. Further, the estimating function 155 is configured to estimate the primary pancreatic duct centerline, by inputting the core point on the centerline of each of the plurality of tubular structure regions extracted with the abovementioned method and the identified positions of the pancreatic proximal site and the pancreatic distal site to the trained model and thus obtaining information about the primary pancreatic duct centerline that is output in response.

In yet another example, the estimating function 155 may estimate the primary pancreatic duct centerline, by referring to a table that keeps the following in correspondence with one another: a core point on the centerline of each of the plurality of tubular structure regions; positions of the pancreatic proximal site; positions of the pancreatic distal site; and information about primary pancreatic duct centerlines. In this situation, the table of the primary pancreatic duct centerlines is generated in advance by using a machine learning method such as deep learning and stored in the memory 120. Further, the estimating function 155 is configured to estimate the primary pancreatic duct centerline by referring to the table stored in the memory 120 so as to obtain information about the primary pancreatic duct centerline that corresponds to the core point on the centerline of each of the plurality of tubular structure regions extracted with the abovementioned method and to the identified positions of the pancreatic proximal site and the pancreatic distal site.

Subsequently, on the basis of the CT image obtained by the obtaining function 151, the generating function 156 generates the CPR image taken along the primary pancreatic duct centerline estimated by the estimating function 155 (step S208 in FIG. 2).

After that, the generating function 156 outputs the generated CPR image to the display 140.

Subsequently, the output function 157 outputs information about the pancreas region extracted by the first extracting function 152 and information about the tubular structure regions extracted by the second extracting function 153 to the display 140 (step S209 in FIG. 2).

More specifically, the output function 157 is configured to output the information about the pancreas region and information about the primary pancreatic duct regions to the display 140 and to a designated output destination. In this situation, the information about the pancreas region includes, for example, the length of the extracted pancreas region (the length of the tube when the pancreas region is assumed to be a tubular structure), the region volume, the area of a region cross-section severed on a cross-cut plane including a line normal to the primary pancreatic duct centerline, as well as the maximum diameter, the minimum diameter, and an average diameter on the area. For example, through a matching process with anatomical landmarks in the surroundings of the pancreas region or with an anatomical model, it is possible to divide the pancreas region into the pancreatic head part (a part enclosed by the aorta and the duodenum), a pancreatic body part (one half positioned on the aorta side when the part interposed between the aorta and the spleen is divided into two in terms of the distance), and the pancreatic tail part (the other half positioned on the spleen side when the part interposed between the aorta and the spleen is divided into two in terms of the distance). In addition to the length, the area, and the volume of the entire pancreas, information about these three parts is also provided. Similarly, the information about the primary pancreatic duct regions also includes, for example, the lengths thereof (the lengths of the centerlines), the volumes, the areas of region cross-sections each severed on a cross-cut plane including a line normal to the primary pancreatic duct centerline, as well as the maximum diameter, the minimum diameter, and an average diameter on each of the areas. The information about the length in the primary pancreatic duct information can be further divided into: the length in which a pancreatic duct was detected, the length in which a pancreatic duct was not detected, and the length in which a pancreatic duct was not detected but interpolated by a computer. With this configuration, when the pancreatic duct was discontinuously detected or failed to be detected, it is possible to output each of the individual lengths and to also display a total length. It is also possible to output calculation values such as an average interruption length, a maximum interruption length, an average continuous length, and/or the like. Further, the information about the primary pancreatic duct regions is also subject to information management, so as to be kept in association with the region of one of the pancreatic head part, the pancreatic body part, and the pancreatic tail part described above.

For example, as the information about the primary pancreatic duct regions, the output function 157 is configured to cause the display 140 to display the information about the extracted centerlines. In that situation, for example, the output function 157 is configured to cause the centerlines to be displayed, either as linear structures alone serving as the extracted results or while being superimposed over an image or the pancreas region. For example, the output function 157 may display the centerlines by using mutually the same color and may display points on the centerlines by using mutually the same symbol. In another example, the output function 157 may be configured to use mutually-different linear shapes, line colors, or symbols for displaying the centerlines which structure the abovementioned primary pancreatic duct centerline candidate and were detected from the tubular structures and for displaying the centerlines estimated (interpolated) by using the method described above (e.g., the centerlines estimated by connecting between the tubular structures or connecting a tubular structure to an end point).

Figures 18A, 18B:
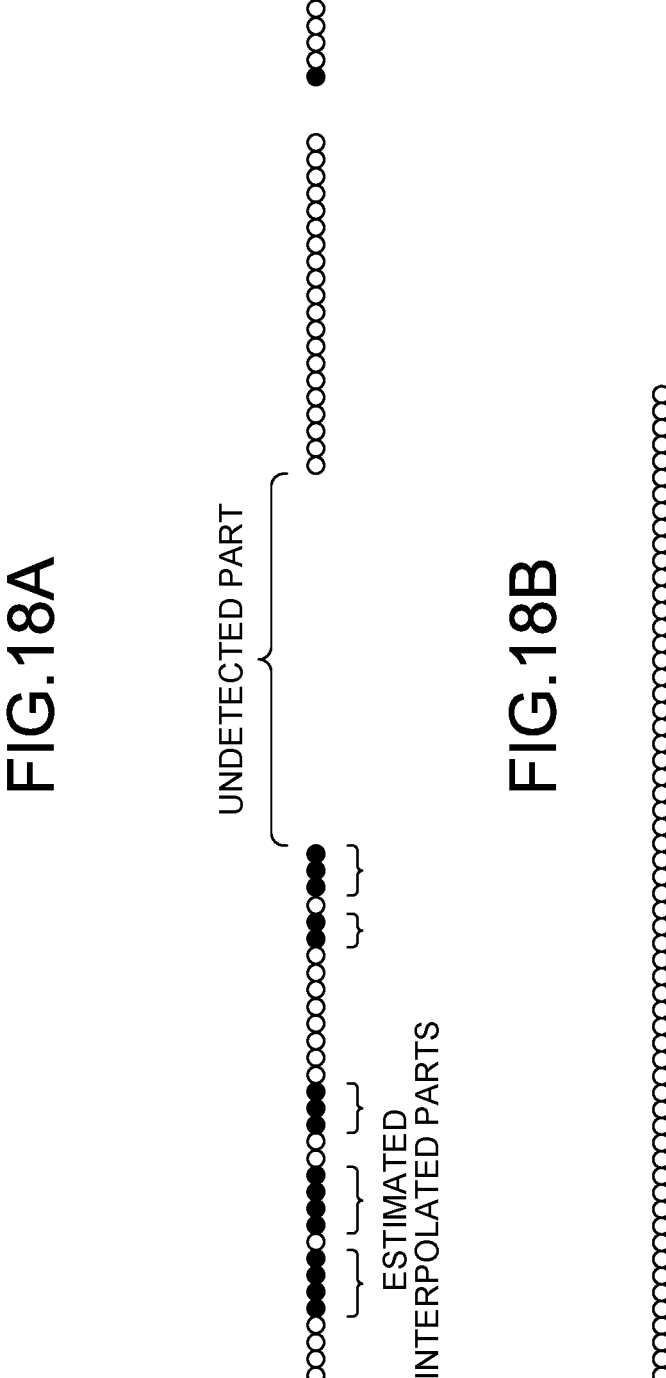
FIGS. 18A and 18B are yet another drawing illustrating the examples of the processes performed by the medical image processing apparatus according to the first embodiment.
Figure 19:
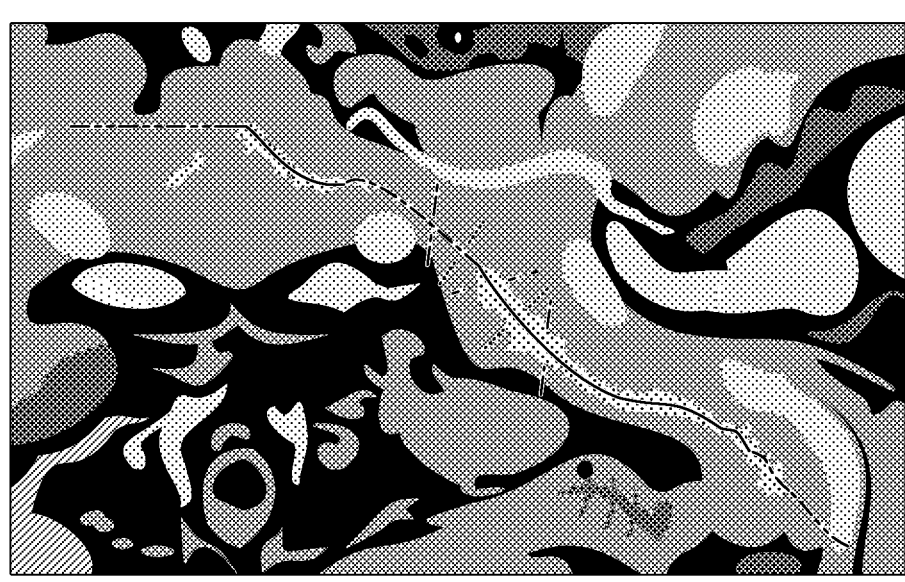
FIG. 19 is yet another drawing illustrating the examples of the processes performed by the medical image processing apparatus according to the first embodiment.

As illustrated in FIGS. 18A and 18B, for example, the output function 157 is configured to display a linear structure representing the centerline. In the example in FIGS. 18A and 18B, the horizontal axis expresses positions in the lengthwise direction, while the white dots represent points on the centerline in the detected parts, the black dots represent points obtained from the speculation based on the preceding and following points (ESTIMATED INTERPO-LATED PARTS), and the blank part represents a position that was not detected (UNDETECTED PART). For example, in the example in FIG. 18A, it is observed that there is a long interruption in a central part of the centerline estimated by using the method described above. Further, in the example in FIG. 18B, it is observed that a centerline is estimated over the entire section of the primary pancreatic duct region. In another example, as illustrated in FIG. 19, the output function 157 may display a linear structure representing the centerline so as to be superimposed over the medical image of the pancreas. In the example in FIG. 19, different parts of the centerline are indicated by using mutually-different linear shapes.

Further, the notifying function 158 outputs a notification about a state of the pancreas to the display 140 in accordance with the information about the pancreas region extracted by the first extracting function 152 and the information about the tubular structure regions extracted by the second extracting function 153 (step S210 in FIG. 2).

For example, the notifying function 158 is configured to output the state of the pancreas to the display 140 in accordance with the length of the pancreas region and the lengths of the tubular structure regions. In this situation, for example, the notifying function 158 is configured to calculate the ratios between the length of the pancreas region extracted by the first extracting function 152 and the length of each of the plurality of tubular structure regions extracted by the second extracting function 153. Further, for example, when there is a tubular structure region of which the calculated ratio exceeds a predetermined threshold value (e.g., 50%), the notifying function 158 is configured to output, to the display 140, information indicating a possibility that the pancreas may be in an abnormal state. For example, together with a message indicating the possibility that the pancreas may be in an abnormal state, the notifying function 158 is configured to output, to the display 140, the length of the entire pancreas region, the lengths of the tubular structure regions, the ratios thereof, and/or the like.

In this situation, when the processing circuitry 150 is realized by using a processor, the process at step S201 in FIG. 2 is realized, for example, as a result of the processing circuitry 150 reading and executing a program corresponding to the obtaining function 151 from the memory 120. Further, the process at step S202 is realized, for example, as a result of the processing circuitry 150 reading and executing a program corresponding to the first extracting function 152 from the memory 120. Also, the process at step S203 is realized, for example, as a result of the processing circuitry 150 reading and executing a program corresponding to the second extracting function 153 from the memory 120. In addition, the process at step S204 is realized, for example, as a result of the processing circuitry 150 reading and executing a program corresponding to the identifying function 154 from the memory 120. Furthermore, the processes at steps S205 through S207 are realized, for example, as a result of the processing circuitry 150 reading and executing a program corresponding to the estimating function 155 from the memory 120. Further, the process at step S208 is realized, for example, as a result of the processing circuitry 150 reading and executing a program corresponding to the generating function 156 from the memory 120. Also, the process at step S209 is realized, for example, as a result of the processing circuitry 150 reading and executing a program corresponding to the output function 157 from the memory 120. In addition, the process at step S210 is realized, for example, as a result of the processing circuitry 150 reading and executing a program corresponding to the notifying function 158 from the memory 120.

As explained above, in the first embodiment, the obtaining function 151 is configured to obtain the CT image related to the pancreas. Further, the first extracting function 152 is configured to extract the pancreas region included in the CT image. Also, the second extracting function 153 is configured to extract at least one tubular structure region from the inside of the pancreas region.

Further, in the first embodiment, the identifying function 154 is configured to identify the pancreatic proximal site and the pancreatic distal site, on the basis of the pancreas region. Also, the estimating function 155 is configured to estimate the primary pancreatic duct centerline of the pancreas, on the basis of the tubular structure regions, the pancreatic proximal site, and the pancreatic distal site. Furthermore, the generating function 156 is configured to generate the CPR image taken along the primary pancreatic duct centerline estimated by the estimating function 155, on the basis of the CT image.

With the configuration described above, even when the primary pancreatic duct rendered in the image is partially interrupted, it is possible to easily set the primary pancreatic duct centerline extending through the entire pancreas. As a result, it is possible to generate the CPR image taken along the extending direction of the primary pancreatic duct, with little trouble, in a short period of time, and with excellent reproducibility.

Further, in the first embodiment, the output function 157 is configured to output the information about the pancreas region and the information about the tubular structure regions. Also, the notifying function 158 is configured to output the notification about the state of the pancreas, in accordance with the information about the pancreas region extracted by the first extracting function 152 and the information about the tubular structure regions extracted by the second extracting function 153.

With the configuration described above, even when the primary pancreatic duct rendered in the image is partially interrupted, it is possible to easily understand the state of the pancreas. For example, when diagnosing processes and examinations are performed for a plurality of patients, the operator such as an image interpreting doctor is able to easily determine which patient should be prioritized in image interpretation.

Consequently, according to the first embodiment, it is possible to easily perform the diagnosing processes and the examinations on the pancreas, even when the primary pancreatic duct rendered in the image is partially interrupted.

The first embodiment has thus been explained. It is also possible to embody the medical image processing apparatus 100 described above while a part of the configuration thereof is modified as appropriate. Thus, in the following sections, modification examples of the first embodiment will be explained as other embodiments. In the embodiments below, differences from the first embodiment will primarily be explained, while detailed explanations of certain duplicate features that have already been explained will be omitted.

Second Embodiment

In the first embodiment described above, for example, the pancreatic proximal site is identified on the basis of the pancreas region extracted from the CT image. However, possible embodiments are not limited to this example. For instance, it is also acceptable to further extract a bile duct region from the CT image and to estimate a primary pancreatic duct centerline by further using the bile duct region. In the following sections, this example will be explained as a second embodiment.

In the present embodiment, the first extracting function 152 is configured to further extract the bile duct region included in the CT image obtained by the obtaining function 151. Further, the estimating function 155 is configured to estimate a bile duct centerline on the basis of the bile duct region extracted by the first extracting function 152 and the tubular structure regions extracted by the second extracting function 153 and to further estimate a primary pancreatic duct centerline of the pancreas further on the basis of the bile duct centerline.

In the following sections, processing functions of the processing circuitry 150 according to the present embodiment will be explained in detail, while referring to specific examples. In the following sections, an example will be explained in which, similarly to the first embodiment, the medical image to be processed is a CT image acquired by an X-ray CT apparatus, while the first end part related to the pancreas is a pancreatic proximal site, whereas the second end part is a pancreatic distal site.

Figure 22:
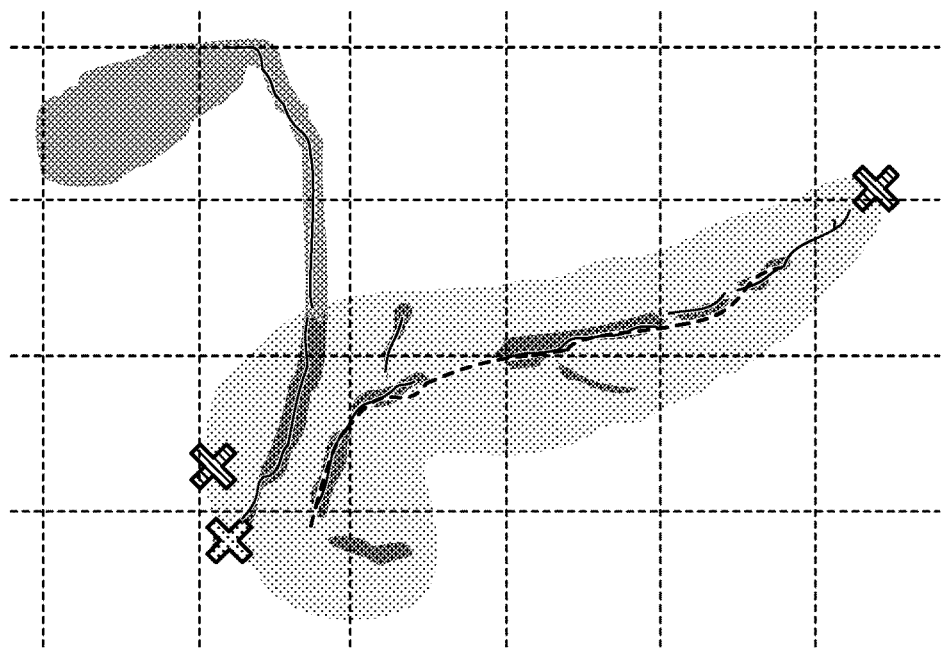
FIG. 22 is another drawing illustrating the examples of the processes performed by the medical image processing apparatus according to the second embodiment.
Figure 23:
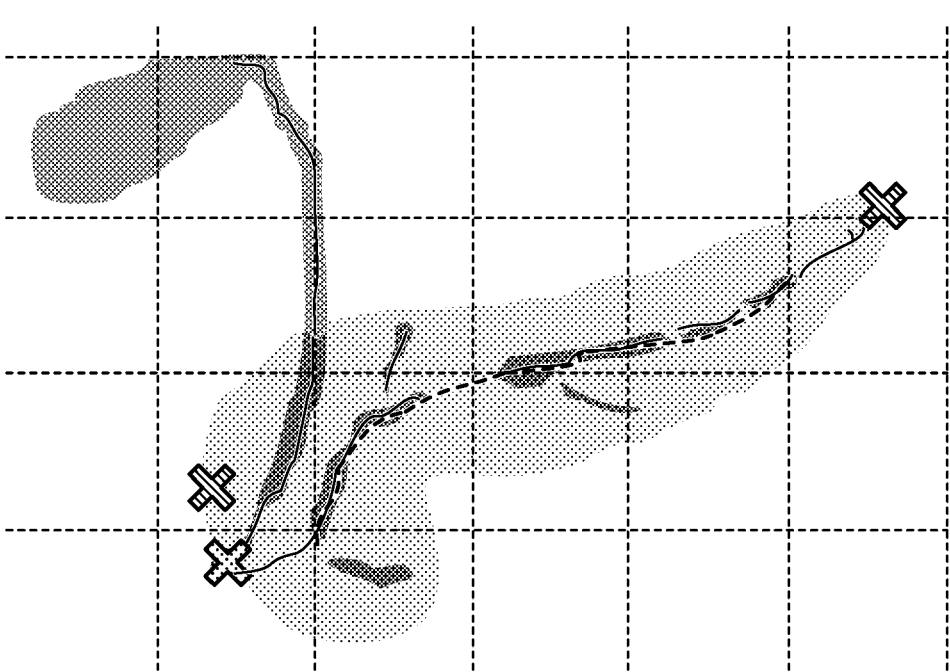
FIG. 23 is yet another drawing illustrating the examples of the processes performed by the medical image processing apparatus according to the second embodiment.

FIG. 20 is a flowchart illustrating a processing procedure in processes performed by the medical image processing apparatus 100 according to the second embodiment. Further, FIGS. 21 to 23 are drawings illustrating examples of the processes performed by the medical image processing apparatus 100 according to the second embodiment.

For example, as illustrated in FIG. 20, in the present embodiment, at first, the obtaining function 151, the first extracting function 152, the second extracting function 153, the identifying function 154, and the estimating function 155 perform the same processes as at steps S201 through S207 described in the first embodiment (steps S301 through S307 in FIG. 20).

Subsequently, the first extracting function 152 extracts the bile duct region included in the CT image obtained by the obtaining function 151 (step S308 in FIG. 20).

Figure 21:
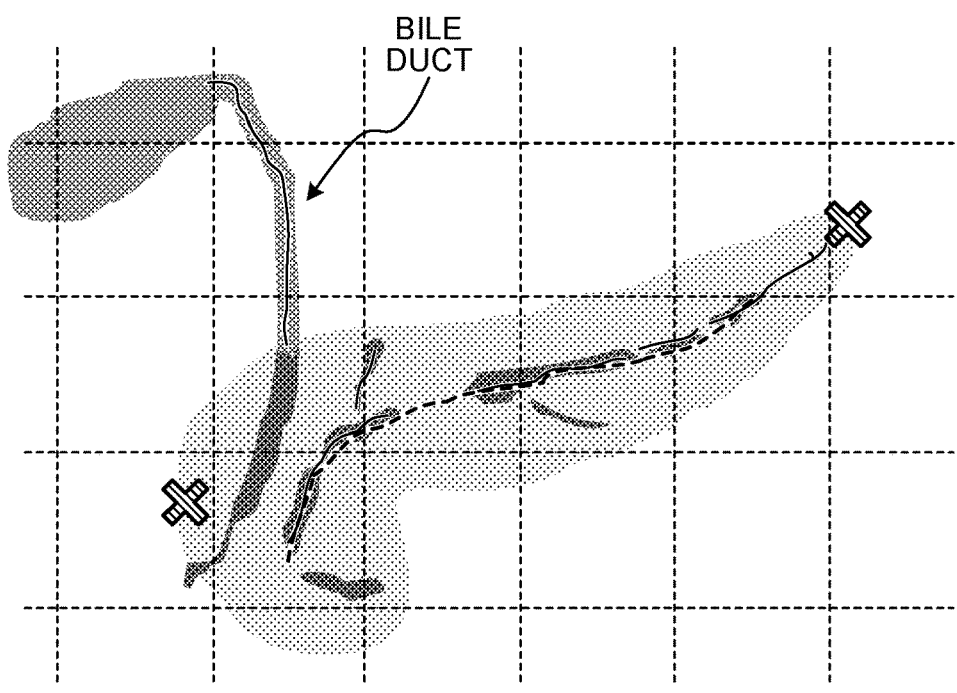
FIG. 21 is a drawing illustrating examples of the processes performed by the medical image processing apparatus according to the second embodiment.

For example, as illustrated in FIG. 21, the first extracting function 152 is configured to extract a tubular structure corresponding to the bile duct, by recognizing either the bile duct or the gallbladder from the CT image. For example, the first extracting function 152 is configured to extract the tubular structure corresponding to the bile duct from the CT image by performing a matching process that uses an anatomical model or anatomical landmarks. Alternatively, for example, the first extracting function 152 may extract the tubular structure corresponding to the bile duct from the CT image by using AI.

Subsequently, the estimating function 155 estimates the bile duct centerline on the basis of the bile duct region extracted by the first extracting function 152 and the tubular structure regions extracted by the second extracting function 153 (step S309 in FIG. 20).

For example, the estimating function 155 is configured to estimate an out-of-pancreas bile duct centerline, by conducting a search toward the legs along the extending direction of the tubular structure corresponding to the bile duct extracted from the CT image.

After that, the estimating function 155 corrects the primary pancreatic duct centerline, by using an end point of the estimated bile duct centerline within the pancreas as a pancreatic proximal site (step S310 in FIG. 20).

For example, as illustrated in FIG. 22, the estimating function 155 is configured to obtain the shortest path that passes through the closest point on the estimated out-of-pancreas bile duct centerline positioned closest to the pancreas region and through a tubular structure region positioned closest to the closest point within the pancreas region and to further estimate the obtained path as the bile duct centerline.

After that, as illustrated in FIG. 23, for example, the estimating function 155 is configured to correct the primary pancreatic duct centerline, by using the end point of the obtained bile duct centerline positioned within the pancreas region as a corrected pancreatic proximal site.

Subsequently, similarly to step S208 described in the first embodiment, the generating function 156 generates a CPR image taken along the primary pancreatic duct centerline corrected by the estimating function 155, on the basis of the CT image obtained by the obtaining function 151 (step S311 in FIG. 20).

Further, the generating function 156 generates a CPR image taken along the bile duct centerline estimated by the estimating function 155, on the basis of the CT image obtained by the obtaining function 151 (step S312 in FIG. 20).

After that, the generating function 156 is configured to output the generated CPR images to the display 140.

Subsequently, similarly to step S209 described in the first embodiment, the output function 157 outputs, to the display 140, the information about the pancreas region extracted by the first extracting function 152 and the information about the tubular structure regions extracted by the second extracting function 153 (step S313 in FIG. 20).

Subsequently, similarly to step S210 described in the first embodiment, the notifying function 158 outputs, to the display 140, a notification about a state of the pancreas, in accordance with the information about the pancreas region extracted by the first extracting function 152 and the information about the tubular structure regions extracted by the second extracting function 153 (step S314 in FIG. 20).

In this situation, when the processing circuitry 150 is realized by using a processor, the process at step S301 in FIG. 20 is realized, for example, as a result of the processing circuitry 150 reading and executing a program corresponding to the obtaining function 151 from the memory 120. Further, the processes at steps S302 and S308 are realized, for example, as a result of the processing circuitry 150 reading and executing a program corresponding to the first extracting function 152 from the memory 120. Also, the process at step S303 is realized, for example, as a result of the processing circuitry 150 reading and executing a program corresponding to the second extracting function 153 from the memory 120. In addition, the process at step S304 is realized, for example, as a result of the processing circuitry 150 reading and executing a program corresponding to the identifying function 154 from the memory 120. Furthermore, the processes at steps S305 through S307, S309, and S310 are realized, for example, as a result of the processing circuitry 150 reading and executing a program corresponding to the estimating function 155 from the memory 120. Further, the processes at steps S311 and S312 are realized, for example, as a result of the processing circuitry 150 reading and executing a program corresponding to the generating function 156 from the memory 120. Also, the process at step S313 is realized, for example, as a result of the processing circuitry 150 reading and executing a program corresponding to the output function 157 from the memory 120. In addition, the process at step S314 is realized, for example, as a result of the processing circuitry 150 reading and executing a program corresponding to the notifying function 158 from the memory 120.

As explained above, in the second embodiment, the first extracting function 152 is configured to further extract the bile duct region included in the CT image. Further, the estimating function 155 is configured to estimate the bile duct centerline on the basis of the bile duct region and the tubular structure regions extracted by the second extracting function 153 and to further estimate the primary pancreatic duct centerline of the pancreas, further on the basis of the bile duct centerline.

With the configuration described above, by estimating the primary pancreatic duct centerline while further using the bile duct region, it is possible to estimate the primary pancreatic duct centerline with a higher level of precision.

Third Embodiment

Further, in the first embodiment described above, for example, only the primary pancreatic duct centerline is estimated; however, possible embodments are not limited to this example. For instance, it is also acceptable to further estimate a secondary pancreatic duct centerline of the pancreas. In the following sections, this example will be explained as a third embodiment.

In the present embodiment, the estimating function 155 is configured to further estimate the secondary pancreatic duct centerline of the pancreas, on the basis of certain tubular structure regions that were not selected as the primary pancreatic duct regions from among the plurality of tubular structure regions extracted by the second extracting function 153.

For example, from among the tubular structure regions that were not selected as the primary pancreatic duct regions, the estimating function 155 is configured to extract a tubular structure region that is positioned in the pancreatic head part (e.g., a region on the smaller coordinates side in terms of the X-axis direction relative to the position of the aorta) and is also positioned in the vicinity of the bile duct within the pancreas region, as a secondary pancreatic duct region. After that, the estimating function 155 is configured to estimate the secondary pancreatic duct centerline by extracting a centerline of the extracted secondary pancreatic duct region.

Subsequently, for example, the generating function 156 is configured to generate a CPR image taken along the secondary pancreatic duct centerline estimated by the estimating function 155, on the basis of the CT image obtained by the obtaining function 151. After that, the generating function 156 is configured to output the generated CPR image to the display 140.

With the configuration described above, it is possible to estimate the secondary pancreatic duct centerline in addition to the primary pancreatic duct centerline. It is therefore possible to perform diagnosing processes and examinations on the pancreas in a diversified manner more easily.

In the first to the third embodiments above, the example was explained in which the medical image to be processed is a CT image; however, possible embodiments are not limited to this example. For instance, the medical image to be processed may be a Magnetic Resonance (MR) image acquired by an MRI apparatus, an ultrasound image obtained by an ultrasound diagnosis apparatus, or an X-ray image obtained by an X-ray diagnosis apparatus.

Further, in the first to the third embodiments above, the example was explained in which the single medical image is used; however, it is also acceptable to use a plurality of mutually-different types of medical images in accordance with purposes. For example, when an MR image is used, it is possible to use a T1-weighted image and a fat suppressed image of the same patient acquired during the same examination, so as to extract a pancreas region from the T1-weighted image, to extract tubular structure regions corresponding to pancreatic ducts from the fat suppressed image, and to further estimate a primary pancreatic duct centerline by integrating the results obtained from those images.

Further, in the first to the third embodiments above, the example was explained in which the pancreatic proximal site and the pancreatic distal site to be used as the first end part and the second end part related to the pancreas are automatically identified from the medical image; however, possible embodiments are not limited to this example. For instance, the identifying function 154 may be configured to receive an operation to designate the pancreatic proximal site and the pancreatic distal site within the medical image, so as to use the pancreatic proximal site and the pancreatic distal site having been designated as the first end part and the second end part.

Further, in the first to the third embodiments above, the example was explained in which the primary pancreatic duct centerline of the pancreas is estimated; however, the above embodiments are also similarly applicable to estimating a centerline of other organs besides the pancreas. For example, it is possible to similarly apply any of the above embodiments to estimating a centerline of a varicose vein in a leg or a centerline of an artery/vein in a finger or a toe.

Furthermore, in the first to the third embodiments above, the example was explained in which the processing circuitry 150 of the medical image processing apparatus 100 includes all of the obtaining function 151, the first extracting function 152, the second extracting function 153, the identifying function 154, the estimating function 155, the generating function 156, the output function 157, and the notifying function 158; however, possible embodiments are not limited to this example. For instance, the medical image processing apparatus 100 described in any of the embodiment may be configured so that the processing circuitry 150 includes the obtaining function 151, the first extracting function 152, the second extracting function 153, the identifying function 154, the estimating function 155, and the generating function 156 or includes the obtaining function 151, the first extracting function 152, the second extracting function 153, the output function 157, and the notifying function 158.

OTHER EMBODIMENTS

Further, the configurations of the medical image processing apparatus 100 in any of the embodiments described above are also applicable to a system mediated by a network, such as a cloud. In that situation, for example, processing circuitry provided in a server apparatus included in the system has installed therein the same functions as those described above, namely, the obtaining function 151, the first extracting function 152, the second extracting function 153, the identifying function 154, the estimating function 155, the generating function 156, the output function 157, and the notifying function 158. Further, the results of the processes performed by the estimating function 155, the generating function 156, the output function 157, and the notifying function 158 are transmitted to a client apparatus used by a user of the system, so as to be displayed on a display included in the client apparatus, or the like.

Further, the configurations of the medical image processing apparatus 100 in any of the embodiments described above are also applicable to a console apparatus of the medical image diagnosis apparatus 1 or to the medical image storage apparatus 2. In that situation, for example, processing circuitry provided in the console apparatus of the medical image diagnosis apparatus 1 or in the medical image storage apparatus 2 has installed therein the same functions as those described above, namely, the obtaining function 151, the first extracting function 152, the second extracting function 153, the identifying function 154, the estimating function 155, the generating function 156, the output function 157, and the notifying function 158.

Furthermore, in the embodiments described above, the processing circuitry does not necessarily have to be realized by using a single processor and may be structured by combining a plurality of independent processors, so that the processing functions are realized as a result of the processors executing the programs. Further, the processing functions of the processing circuitry may be realized as being distributed among or integrated into one or more pieces of processing circuitry, as appropriate. Further, the processing functions of the processing circuitry may be realized by using a combination of hardware such as circuitry and software. Further, although the example was explained in which the programs corresponding to the processing functions are stored in the single memory element, possible embodiments are not limited to this example. For instance, the programs corresponding to the processing functions may be stored in a plurality of memory elements in a distributed manner, while the processing circuitry is configured to read and execute the programs from the memory elements.

Further, in the embodiments described above, the example was explained in which an obtaining unit, a first extracting unit, a second extracting unit, an identifying unit, an estimating unit, a generating unit, and a notifying unit of the present disclosure are realized by using the obtaining function 151, the first extracting function 152, the second extracting function 153, the identifying function 154, the estimating function 155, the generating function 156, the output function 157, and the notifying function 158 of the processing circuitry 150, respectively; however, possible embodiments are not limited to this example. For instance, instead of being realized by using the obtaining function 151, the first extracting function 152, the second extracting function 153, the identifying function 154, the estimating function 155, the generating function 156, the output function 157, and the notifying function 158 described in the embodiments, the functions of the obtaining unit, the first extracting unit, the second extracting unit, the identifying unit, the estimating unit, the generating unit, and the notifying unit of the present disclosure may be realized by using hardware alone, software alone, or a combination of hardware and software.

Further, the term "processor" used in the above description of the embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). In this situation, instead of having the programs saved in the memory, it is also acceptable to directly incorporate the programs into the circuitry of one or more processors. In that situation, the one or more processors realize the functions by reading and executing the programs incorporated in the circuitry thereof. Further, the processors of any of the present embodiments do not each necessarily have to be structured as a single circuit. It is also acceptable to structure one processor by combining together a plurality of independent circuits so as to realize the functions thereof.

In this situation, the programs executed by the one or more processors are provided as being incorporated, in advance, in a Read Only Memory (ROM), a memory, or the like. Also, the programs may be provided as being recorded in a non-transitory computer-readable storage medium such as a Compact Disk Read-Only Memory (CD-ROM), a Flexible Disk (FD), a Compact Disk Recordable (CD-R), a Digital Versatile Disk (DVD), or the like, in a file in a format that is installable or executable by these devices. Further, the programs may be stored in a computer connected to a network such as the Internet so as to be provided or distributed as being downloaded via the network. For example, the programs are structured with modules including the processing functions described above. In the actual hardware, as a result of a CPU reading and executing the programs from a storage medium such as a ROM, the modules are loaded into a main storage device and generated in the main storage device.

Furthermore, the constituent elements of the apparatuses in the drawings of the above embodiments are based on functional concepts. Thus, it is not necessarily required to physically configure the constituent elements as indicated in the drawings. In other words, specific modes of distribution and integration of the apparatuses are not limited to those illustrated in the drawings. It is acceptable to functionally or physically distribute or integrate all or a part of the apparatuses in any arbitrary units, depending on various loads, the status of use, and the like. In addition, all or an arbitrary part of the processing functions performed by the apparatuses may be realized by a CPU and a program analyzed and executed by the CPU or may be realized as hardware using wired logic.

With regard to the processes explained in the above embodiments, it is acceptable to manually perform all or a part of the processes described as being performed automatically. Conversely, by using a publicly-known method, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

Further, various types of data handled in the present disclosure are, typically, digital data.

According to at least one aspect of the embodiments described above, it is possible to easily perform diagnosing processes and examinations on the pancreas, even when the primary pancreatic duct rendered in an image is partially interrupted.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

In relation to the embodiments described above, as certain aspects and selective characteristics of the present disclosure, the following notes are provided:

Note 1:

A medical image processing apparatus, comprising:

an obtaining unit configured to obtain a medical image related to a pancreas;

a first extracting unit configured to extract a pancreas region included in the medical image;

a second extracting unit configured to extract at least one tubular structure region from the inside of the pancreas region;

an identifying unit configured to identify a first end part and a second end part related to the pancreas on the basis of the pancreas region; and an estimating unit configured to estimate a primary pancreatic duct centerline of the pancreas on the basis of the tubular structure region, the first end part, and the second end part.

Note 2:

The first extracting unit may be configured to further extract a bile duct region included in the medical image, and the estimating unit may be configured to estimate a bile duct centerline on the basis of the bile duct region and the tubular structure region and to estimate the primary pancreatic duct centerline further on the basis of the bile duct centerline.

Note 3:

The first end part may be a pancreatic proximal site, whereas the second end part may be a pancreatic distal site.

Note 4:

The first end part may be a pancreatic proximal site, whereas the second end part may be a pancreatic distal site, and the estimating unit may be configured to correct the primary pancreatic duct centerline, by using an end point of the bile duct centerline within the pancreas as the pancreatic proximal site.

Note 5:

The second extracting unit may be configured to extract a plurality of tubular structure regions including the abovementioned tubular structure region, from the inside of the pancreas region, and the estimating unit may be configured to select, from among the plurality of tubular structure regions, a plurality of tubular structure regions in the vicinity of the center of the pancreas region as primary pancreatic duct regions and to estimate the primary pancreatic duct centerline on the basis of the primary pancreatic duct regions, the first end part, and the second end part.

Note 6:

The estimating unit may be configured to estimate the primary pancreatic duct centerline, by setting a path that passes through the vicinity of the center of each of the plurality of tubular structure regions selected to be the primary pancreatic duct regions as a primary pancreatic duct centerline candidate and further linking together the primary pancreatic duct centerline candidate, a path that connects one end of the primary pancreatic duct centerline candidate to the first end part, and a path that connects the other end of the primary pancreatic duct centerline candidate to the second end part.

Note 7:

the estimating unit may be configured to set, when the path that passes through the vicinity of the center of each of the plurality of tubular structure regions selected to be the primary pancreatic duct regions has a tree-like structure having a plurality of branches, a longest branch extending in a direction connecting the first end part to the second end part within the tree-like structure, as the primary pancreatic duct centerline candidate.

Note 8:

The estimating unit may be configured to further estimate a secondary pancreatic duct centerline of the pancreas, on the basis of one or more tubular structure regions that were not selected as the primary pancreatic duct regions from among the plurality of tubular structure regions.

Note 9:

The medical image processing apparatus may further include: a generating unit configured to generate a Curved Planar Reconstruction (CPR) image taken along the primary pancreatic duct centerline, on the basis of the medical image.

Note 10:

An output unit configured to output information about the pancreas region and information about the tubular structure region may further be provided.

Note 11:

The medical image processing apparatus may further include: a notifying unit configured to output a notification about a state of the pancreas, in accordance with information about the pancreas region and information about the tubular structure region.

Note 12:

A medical image processing apparatus, comprising:

an obtaining unit configured to obtain a medical image related to a pancreas;

a first extracting unit configured to extract a pancreas region included in the medical image;

a second extracting unit configured to extract at least one tubular structure region from the inside of the pancreas region; and a notifying unit configured to output a notification about a state of the pancreas, in accordance with information about the pancreas region and information about the tubular structure region.

Note 13:

A medical image processing method, comprising:

a step of obtaining a medical image related to a pancreas;

a step of extracting a pancreas region included in the medical image;

a step of extracting at least one tubular structure region from the inside of the pancreas region;

a step of identifying a first end part and a second end part related to the pancreas on the basis of the pancreas region; and a step of estimating a primary pancreatic duct centerline of the pancreas on the basis of the tubular structure region, the first end part, and the second end part.

Note 14:

A medical image processing method, comprising:

a step of obtaining a medical image related to a pancreas;

a step of extracting a pancreas region included in the medical image;

a step of extracting at least one tubular structure region from the inside of the pancreas region; and a step of outputting a notification about a state of the pancreas, in accordance with information about the pancreas region and information about the tubular structure region.

Note 15:

A medical image processing program, comprising instructions for causing a computer to perform:

a procedure of obtaining a medical image related to a pancreas;

a procedure of extracting a pancreas region included in the medical image;

a procedure of extracting at least one tubular structure region from the inside of the pancreas region;

a procedure of identifying a first end part and a second end part related to the pancreas on the basis of the pancreas region; and a procedure of estimating a primary pancreatic duct centerline of the pancreas on the basis of the tubular structure region, the first end part, and the second end part.

Note 16:

A medical image processing program, comprising instructions for causing a computer to perform:

a procedure of obtaining a medical image related to a pancreas;

a procedure of extracting a pancreas region included in the medical image;

a procedure of extracting at least one tubular structure region from the inside of the pancreas region; and a procedure of outputting a notification about a state of the pancreas, in accordance with information about the pancreas region and information about the tubular structure region.

What is claimed is:

1. A medical image processing apparatus, comprising:
processing circuitry configured to obtain a medical image related to a pancreas;

extract a pancreas region included in the medical image;

extract a plurality of tubular structure regions from an inside of the extracted pancreas region;

identify a first end part and a second end part related to the pancreas based on the pancreas region;

select, from among the plurality of tubular structure regions, a plurality of primary tubular structure regions in a vicinity of a center of the pancreas region, detect a centerline of each of the selected tubular structure regions as a first centerline, estimate a path that connects the first centerlines between each of the tubular structure regions as a second centerline, set a primary pancreatic duct centerline candidate by connecting the first centerlines with the second centerline, and estimate a primary pancreatic duct centerline of the pancreas by linking together the primary pancreatic duct centerline candidate a path that connects one end of the primary pancreatic duct centerline candidate to the first end part, and a path that connects the other end of the primary pancreatic duct centerline candidate to the second end part;

cause the estimated primary pancreatic duct centerline including the first centerlines and the second centerlines to be displayed on a display as a linear structure, wherein the primary pancreatic duct centerline is displayed while being superimposed over the medical image and the pancreas region, and the first centerlines and the second centerlines are displayed in a different mode; and calculate ratios between a length of the pancreas region and a length of each of the plurality of tubular structure regions and when there is a tubular structure region of which the calculated ratio exceeds a predetermined threshold value, cause a length of the pancreas region, a length of the tubular structure region, and the ratio to be displayed further on the display together with a message indicating a possibility that the pancreas may be in an abnormal state.

2. The medical image processing apparatus according to claim 1, wherein the processing circuitry is further configured to:

extract a bile duct region included in the medical image, and estimate a bile duct centerline based on the bile duct region and the plurality of tubular structure regions, and estimate the primary pancreatic duct centerline further based on the bile duct centerline.

3. The medical image processing apparatus according to claim 1, wherein the first end part is a pancreatic proximal site, whereas the second end part is a pancreatic distal site.

4. The medical image processing apparatus according to claim 2, wherein the first end part is a pancreatic proximal site, whereas the second end part is a pancreatic distal site, and the processing circuitry is further configured to correct the primary pancreatic duct centerline, by using an end point of the bile duct centerline within the pancreas as the pancreatic proximal site.

5. The medical image processing apparatus according to claim 1, wherein the processing circuitry is further configured to set, when a path obtained by connecting the first center lines with the second center lines has a tree-like structure having a plurality of branches, a longest branch extending in a direction connecting the first end part to the second end part within the tree-like structure, as the primary pancreatic duct centerline candidate.

6. The medical image processing apparatus according to claim 1, wherein the processing circuitry is further configured to estimate a secondary pancreatic duct centerline of the pancreas, based on one or more tubular structure regions that were not selected from among the plurality of tubular structure regions.

7. The medical image processing apparatus according to claim 1, wherein the processing circuitry is further configured to generate a Curved Planar Reconstruction (CPR) image taken along the primary pancreatic duct centerline, based on the medical image.

8. The medical image processing apparatus according to claim 1, wherein the processing circuitry is further configured to output a notification about a state of the pancreas, in accordance with information about the pancreas region and information about the tubular structure region.

9. A medical image processing method, comprising:

obtaining a medical image related to a pancreas;

extracting a pancreas region included in the medical image;

extracting a plurality of tubular structure regions from an inside of the pancreas region;

identifying a first end part and a second end part related to the pancreas based on the pancreas region;

selecting, from among the plurality of tubular structure regions, a plurality of primary tubular structure regions in a vicinity of a center of the pancreas region, detecting a centerline of each of the selected tubular structure regions as a first centerline, estimating a path that connects the first centerlines between each of the tubular structure regions as a second centerline setting a primary pancreatic duct centerline candidate by connecting the first centerlines with the second centerlines, and estimating a primary pancreatic duct centerline of the pancreas by linking together the primary pancreatic duct centerline candidate a path that connects one end of the primary pancreatic duct centerline candidate to the first end part, and a path that connects the other end of the primary pancreatic duct centerline candidate to the second end part;

causing the estimated primary pancreatic duct centerline including the first centerlines and the second centerlines to be displayed on a display as a linear structure, wherein the primary pancreatic duct centerline is displayed while being superimposed over the medical image and the pancreas region, and the first centerlines and the second centerlines are displaced in a different mode; and calculating ratios between a length of the pancreas region and a length of each of the plurality of tubular structure regions, and, when there is a tubular structure region of which the calculated ratio exceeds a predetermined threshold value, causing a length of the pancreas region, a length of the tubular structure region, and the ratio to be displayed further on the display together with a message indicating a possibility that the pancreas may be in an abnormal state.

10. A non-transitory computer-readable storage medium having stored therein a plurality of computer-executable instructions for causing a computer to execute:

obtaining a medical image related to a pancreas;

extracting a pancreas region included in the medical image;

extracting a plurality of tubular structure regions from an inside of the pancreas region;

identifying a first end part and a second end part related to the pancreas based on the pancreas region;

selecting, from among the plurality of tubular structure regions, a plurality of primary tubular structure regions in a vicinity of a center of the pancreas region, detecting a centerline of each of the selected tubular structure regions as a first centerline, estimating a path that connects the first centerlines between each of the tubular structure regions as a second centerline, setting a primary pancreatic duct centerline candidate by connecting the first centerlines with the second centerlines, and estimating a primary pancreatic duct centerline of the pancreas by linking together the primary pancreatic duct centerline candidate, a path that connects one end of the primary pancreatic duct centerline candidate to the first end part, and a path that connects the other end of the primary pancreatic duct centerline candidate to the second end part;

causing the estimated primary pancreatic duct centerline including the first centerlines and the second centerlines to be displayed on a display as a linear structure, wherein the primary pancreatic duct centerline is displayed while being superimposed over the medical image and the pancreas region, and the first centerlines and the second centerlines are displayed in a different mode; and calculating ratios between a length of the pancreas region and a length of each of the plurality of tubular structure regions, and when there is a tubular structure region of which the calculated ratio exceeds a predetermined threshold value, causing a length of the pancreas region, a length of the tubular structure region, and the ratio to be displayed further on the display together with a message indicating a possibility that the pancreas may be in an abnormal state.

* * * * *